(12) United States Patent
Dussarrat et al.

(10) Patent No.: US 10,106,568 B2
(45) Date of Patent: Oct. 23, 2018

(54) HAFNIUM-CONTAINING FILM FORMING COMPOSITIONS FOR VAPOR DEPOSITION OF HAFNIUM-CONTAINING FILMS

(71) Applicant: L'Air Liquide, Société Anonyme pour l'Etude et l'Exploitation des Procédés Georges Claude, Paris (FR)

(72) Inventors: Christian Dussarrat, Tokyo (JP); Jean-Marc Girard, Versailles (FR); Hana Ishii, Tsukuba (JP); Clément Lansalot-Matras, Princeton, NJ (US); Julien Lieffrig, Soucy (FR)

(73) Assignee: L'Air Liquide, Société Anonyme pour l'Etude et l'Exploitation des Procédés Georges Claude, Paris (FR)

(*) Notice: Subject to any disclaimer, the term of this patent is extended or adjusted under 35 U.S.C. 154(b) by 0 days.

(21) Appl. No.: 15/337,840

(22) Filed: Oct. 28, 2016

(65) Prior Publication Data

US 2017/0044199 A1 Feb. 16, 2017

(51) Int. Cl.
| C07F 17/00 | (2006.01) |
| H01L 27/108 | (2006.01) |
| H01L 21/285 | (2006.01) |
| B05D 1/00 | (2006.01) |

(52) U.S. Cl.
CPC ............... *C07F 17/00* (2013.01); *B05D 1/60* (2013.01); *B05D 1/62* (2013.01); *H01L 21/285* (2013.01); *H01L 27/108* (2013.01)

(58) Field of Classification Search
None
See application file for complete search history.

(56) References Cited

U.S. PATENT DOCUMENTS

| | | | |
|---|---|---|---|
| 4,931,417 A | 6/1990 | Miya et al. | |
| 5,360,921 A * | 11/1994 | Kiso ................. | C07F 7/0827 556/478 |
| 5,527,752 A | 6/1996 | Reichle et al. | |
| 5,846,895 A | 12/1998 | Gila et al. | |
| 5,861,352 A | 1/1999 | Gila et al. | |
| 6,001,742 A | 12/1999 | Chang | |
| 6,197,683 B1 | 3/2001 | Kang et al. | |
| 6,268,448 B1 | 7/2001 | Collins et al. | |
| 6,445,023 B1 | 9/2002 | Vaartstra et al. | |
| 6,548,424 B2 | 4/2003 | Putkonen | |
| 6,669,990 B2 | 12/2003 | Min et al. | |
| 6,689,675 B1 | 2/2004 | Parker et al. | |
| 6,743,473 B1 | 6/2004 | Parkhe et al. | |
| 6,858,547 B2 | 2/2005 | Metzner et al. | |
| 6,984,591 B1 | 1/2006 | Buchanan et al. | |
| 7,108,747 B1 | 9/2006 | Leskela et al. | |
| 9,499,571 B2 * | 11/2016 | Lansalot-Matras ..... | C07F 7/006 |

(Continued)

FOREIGN PATENT DOCUMENTS

| EP | 1 067 595 | 1/2001 |
| EP | 1 524 299 | 4/2005 |

(Continued)

OTHER PUBLICATIONS

Beachley, O. T. et al., "Reagents based on cyclopentadienyl derivatives of the Group 14 elements for the synthesis of indium(I) derivatives. Crystal and molecular structure of in(C5H4SiMe3)," Organometallics 1990, 9, 2488-2492.
Becker, J.S. et al., "Atomic layer deposition of hafnium and zirconium nitrides", Chem. Mater. 2004, 16, 3497-3501.
Boscherini, F. et al., "Atomic scale mechanism for the Ge-induced stabilization of the tetragonal, very high-k phase of ZrO2," Applied Physics Letters 99, 121909 (2011).
Bürger, H. et al., "Titan-Stickstoff-Verbindungengen, Darstellung und Eigenschaften Substituierter Cyclopentadienyl-Titan-Dialkylamide," Journal of Organometallic Chemistry, 101 (1975) 295-306.
Cano, J. et al., "Neutral and cationic [bis(n1-amidosilyl)-n5-cyclopentadienyl]titanium and -zirconium complexes: synthesis, x-ray molecular structures and DFT calculations", Eur. J. Inorg. Chem. 2003, 2463-2474.

(Continued)

*Primary Examiner* — Clinton A Brooks
(74) *Attorney, Agent, or Firm* — Patricia E. McQueeney

(57) ABSTRACT

Disclosed are Hafnium-containing film forming compositions comprising Silicon- and Hafnium-containing precursors having one of the following formula:

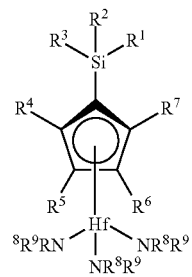

Formula I

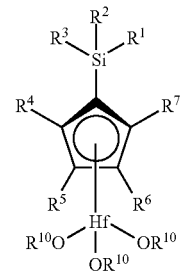

Formula II wherein each $R^1$, $R^2$, $R^3$, $R^4$, $R^5$, $R^6$, $R^7$, $R^8$, $R^9$ and $R^{10}$ is independently selected from H; a C1-C5 linear, branched, or cyclic alkyl group; or a C1-C5 linear, branched, or cyclic fluoroalkyl group. Also disclosed are methods of synthesizing the disclosed compositions and using the same to deposit Hafnium-containing thin films on substrates via vapor deposition processes.

15 Claims, 1 Drawing Sheet

(56) References Cited

U.S. PATENT DOCUMENTS

| | | | |
|---|---|---|---|
| 2001/0001949 | A1 | 5/2001 | Westmoreland et al. |
| 2004/0235312 | A1 | 11/2004 | Loftin et al. |
| 2005/0056219 | A1 | 3/2005 | Dip et al. |
| 2005/0260357 | A1 | 11/2005 | Olsen et al. |
| 2006/0062917 | A1 | 3/2006 | Muthukrishnan et al. |
| 2006/0097305 | A1 | 5/2006 | Lee |
| 2006/0228888 | A1 | 10/2006 | Lee et al. |
| 2008/0308793 | A1 | 12/2008 | Jeong et al. |
| 2009/0203222 | A1 | 8/2009 | Dussarrat et al. |
| 2009/0311879 | A1 | 12/2009 | Blasco et al. |
| 2013/0208403 | A1 | 8/2013 | Rocklein et al. |
| 2015/0110958 | A1* | 4/2015 | Lansalot-Matras ..... C07F 7/006 427/253 |
| 2015/0176120 | A1 | 6/2015 | Lansalot-Matras et al. |

FOREIGN PATENT DOCUMENTS

| | | | |
|---|---|---|---|
| JP | H11 307519 | 11/1999 | |
| JP | 2001 102326 | 4/2001 | |
| JP | 2001 355070 | 12/2001 | |
| JP | 2002 069641 | 3/2002 | |
| JP | 2002 093803 | 3/2002 | |
| JP | 2002 093804 | 3/2002 | |
| JP | 2004 507551 | 3/2004 | |
| JP | 2004 300579 | 10/2004 | |
| JP | 2004 34970 | 12/2004 | |
| JP | 2005 104994 | 4/2005 | |
| JP | 2005 171291 | 6/2005 | |
| JP | 2005 209766 | 8/2005 | |
| KR | 2008 0101040 | 11/2008 | |
| KR | 10 1284664 | 7/2012 | |
| KR | 101284664 | * 7/2013 | ................ C07F 7/00 |
| WO | WO 96 27032 | 9/1996 | |
| WO | WO 97 49105 | 12/1997 | |
| WO | WO 02 18394 | 3/2002 | |
| WO | WO 03 035926 | 5/2003 | |
| WO | WO 2004 010469 | 1/2004 | |
| WO | WO 2005 113852 | 12/2005 | |
| WO | WO 2007 141059 | 6/2006 | |
| WO | WO 2006 131751 | 12/2006 | |
| WO | WO 2007 005088 | 1/2007 | |
| WO | WO 2007 011973 | 1/2007 | |
| WO | WO 2007 030673 | 3/2007 | |
| WO | WO 2007 066546 | 6/2007 | |
| WO | WO 2007 140813 | 12/2007 | |
| WO | WO 2009 036046 | 3/2009 | |
| WO | WO 2009 087609 | 7/2009 | |
| WO | WO 2009 106433 | 9/2009 | |
| WO | WO 2011 020042 | 2/2011 | |

OTHER PUBLICATIONS

Carta, G. et al., "Thermal properties of volatile organohafnium precursors for $HfO_2$ MOCVD processes," Electrochemical Society Proceedings vol. 2005-09, 260-267.

Caymax, M. et al., "High-k materials for advanced gate stack dielectrics: a comparison of ALCVD and MOCVD as deposition technologies," 2003 Materials Research Society Symposium Proceedings, vol. 765, 47-58.

Chandra, G. et al. "Amido-derivatives of metals and metalloids. Part VI. Reactions of titanium(IV), zirconium(IV), and hafnium(IV) amides with protic compounds," Journal of Chemical Society (A), 1968, 1940-1945.

Chang, H.S. et al. "Electrical and physical properties of $HfO_2$ deposited via ALD using $Hf(OtBu)_4$ and ozone atop $Al_2O_3$," Electrochem. Solid-State Letters, 7 (6) (2004), F42-F44.

Chung, Y.J. et al., Trimethylsilylcyclopentadienyl tris(dimethylamino)zirconium as a single-source metal precursor for the atomic layer deposition of $Zrr_xSi_{1-x}O_4$, Thin Solid Films 564 (2014), 140-145.

Ciruelo, G. et al., "Synthesis and reactivity of new silyl substituted monocyclopentadienyl zirconium complexes. X-ray molecular structure of $[Zr(N^5-C_5H_4(SiMe_2CH_2Ph))(CH_2Ph)_3]$", Journal of Organometallic Chemistry 547 (1997), 287-296.

Codato, S. et al. "MOCVD growth and characterization of $ZrO_2$ thin films obtained from unusual organo-zirconium precursors," Chemical Vapor Deposition, Wiley-VCh Verlag, Weinheim, Germany, vol. 11, No. 11, 1999, 159-164.

Cotton, S.A. "Ti, Ar, Hf," Annu. Rep.Prog. Chem., Sect. A: Inorganic Chemistry, 1993, 90, 119-130.

Gilmore, C. M. et al., "Stabilized zirconia-alumina thin films," J. Vac. Sci. Technol. A 4, 2598, Nov./Dec. 1986.

Hausmann, D.M. et al. "Atomic layer deposition of hafnium and zirconium oxide using metal amide precursors," Chem., Mater. 2002, 14, 4350-4353.

Herrmann, W.A. et al., "Volatile metal alkoxides according to the concept of donor functionalization," Angew. Chem. Int. Ed. Engl. 1995, 34, 2187-2206.

Irigoyen, A.M. et al., Synthesis and characterization of chlorobis(dialkylamido) and alkylbis(dialkylamido) derivatives of $[(n^5-C_5Me_5)MCl_3](M=Ti, Zr)$, Journal of Organometallic Chemistry, 494 (1995) 255-259.

Juppo, M. et al. "In situ mass spectrometry study on surface reactions in atomic layer deposition of $Al_2O_3$ thin films from trimethylaluminum and water," Langmuir 2000, 16, 4034-4039.

Jutzi, P. et al., "Halbsandwich-Komplexe der Elemente Titan und Zirconium mit dem (Diisopropylaminoethyl) cyclopentadienyl-Ligand: Molekülstruktur von $[(C_5H_4CH_2CH_2N(H)^iPr_2)ZrCl_3]^+Cl^-\cdot 2CH_3OH$", Journal of Organometallic Chemistry 533 (1997), 237-245.

Kawahara, T. et al. "Effect of Hf source, oxidizing agents, and $NH_3$/Ar plasma on the properties of $HfAlO_x$ films prepared by atomic layer deposition," J. Appl. Phys., vol. 43, No. 7A, 2004, 4129-4134.

Khojier, K. et al., "Structural, electrical, and decorative properties of sputtered zirconium thin films during post-annealing process," Journal of Theoretical and Applied Physics 2013, 7:55, 1-7.

Kim, M.-S. et al., "ALD analyses of HfCl4 + O3 and HfCl4 + H2O by mass spectroscopy," Electrochemical Society Proceedings vol. 2005-05, 397-403.

Kittl, J.A. et al., "High-k dielectrics for future generation memory devices," Microelectronic Engineering 86 (2009) 1789-1795.

Kukli, K. et al., "Atomic layer deposition of hafnium dioxide films from 1-methoxy-2-methyl-2-propanolate complex of hafnium," Chem Mater. 2003, 15, 1722-1727.

Kukli, K. et al., "Influence of growth temperature on properties of zirconium dioxide films grown by atomic layer deposition," Journal of Applied Physics, 2002, 92, p. 1833-1840.

Lehn, J.-S. et al., "New precursors for the DVD of zirconium and hafnium oxide films," Chem Vap. Deposition 2006, 12, 280-284.

Miikkulainen, V. et al., "Crystallinity of inorganic films grown by atomic layer deposition: overview and general trends," Applied Physics Reviews (2012) Version Sep. 14, 2012, 1-92.

Niinistö, J. et al., "Development of novel processes for atomic layer deposition of high-k dielectrics", $72^{nd}$ Annual Meeting of the DPG, Feb. 27 2008, Berlin.

Niinistö, J. et al. "In situ quadrupole mass spectrometry study of atomic-layer deposition of $ZrO_2$ using $Cp_2Zr(CH_3)_2$ and water," Langmuir, 7321, 21, 2005.

Niinistö, J. et al., "Novel mixed alkylamido-cyclopentadienyl precursors for ALD of ZrO2 thin films," J. Mater. Chem., 2008, 18, 5243-5247.

Pinchart, A. et al., "Novel thermally-stable hafnium and zirconium ALD precursors", IEEE/SEMI Advanced Semiconductor Manufacturing Conference (ASMC) 2007.

Potter, R.J. et al., "Deposition of $HfO_2$, $Gd_2O_3$ and $PrO_x$ by liquid injection ALD techniques," Chem. Vap. Deposition 2005, 11, No. 3, 159-169.

Putkonen, M. et al., "Organometallic precursors for atomic layer deposition," Top Organomet Chem, 2005, 9, 125-145.

Putkonen, M. et al. "Zirconia thin films by atomic layer epitaxy. A comparative study on the use of novel precursors with ozone," J. Mater. Chem., 3141, 11, 2001.

Qian, X. et al., "Synthesis of new substituted cyclopentadienyl titanium monomethoxydifluorides with $BF_3\cdot OEt_2$ as fluorinating reagent and their use in syndiotactic polymerization of styrene," Journal of Organometallic Chemistry 689 (2004), 1503-1510.

(56) References Cited

OTHER PUBLICATIONS

Rahmani, S. et al., "Preparation of tethered half-titanocene complex on syndiotactic poly(styrene-co-p-methylstyrene) for using in syndiospecific polymerization of styrene," Catal Lett (2011) 141, 1625-1634.

Rie, K.-T. et al., "Plasma assisted CVD for low temperature coatings to improve the wear and corrosion resistance," Surface and Coatings Technology, 1996, 86-87, 498-506.

Ritala, M. et al., "Atomic layer deposition," Ch. 2, Handbook of Thin Film Materials, H.S. Nalwa, ed., vol. 1, "Deposition and Processing of Thin Films," Academic Press, San Diego, CA, 2002.

Rogers, J.S. et al. "Fulvene to cyclopentadienyl conversion with homoleptic complexes of zirconium and hafnium", Organometallics 1999 18, 3976-3980.

Schneider, H. et al. "Immobilization of $\eta^5$-cyclopentadienyltris(dimethylamido)zirconium polymerization catalysts on a chlorosilane- and HMDS-modified mesoporous silica surface: A new concept for supporting metallocene amides towards heterogenous single-site-catalysts," Journal of Molecular Catalysts A; Chemical 170 (2001) 127-141.

Senzaki, Y. et al. "Atomic layer deposition of hafnium oxide and hafnium silicate thin films using liquid precursors and ozone," J. Vac. Sci. Technol. A 22(4), Jul./Aug. 2004.

Tsoutsou, D. et al., "Stabilization of very high-$k$ tetragonal phase in Ge-doped ZrO2 films grown by atomic oxygen beam deposition," J. Appl. Phys. 106 (2009), 024107.

Tsoutsou, D. et al., "Stabilization of a very high-k tetragonal ZrO2 phase by direct doping with germanium," Microelectronic Engineering 86 (2009), 1626-1628.

Triyoso, D.H. et al. "Physical and electrical characteristics of $HfO_2$ gate dielectrics deposited by ALD and MOCVD," J. Electrochem. Soc., 152 (3) (2005), G203-G209.

Vanderbilt, D. et al., "Structural and dielectric properties of crystalline and amorphous ZrO2," Thin Solid Films 486 (2005), 125-128.

Vollmerhaus, R. et al., "Synthesis and structure of Group 4 iminophosphonamide complexes," Organometallics, 2005, vol. 24, 494-507.

Williams P.A. et al., "Novel mononuclear alkoxide precursors for the MOCVD of ZrO2 and HfO2 thin films," Chem Vap. Deposition 2002, 8, No. 4, 163-170.

Winter, C.H. et al., "Metallic materials deposition: metal-organic precursors," Encyclopedia of Inorganic Chemistry, 2006, John Wiley & Sons Ltd., DOI: 10.1002/ 0470862106.ia138.

Wu, Y-H.et al., "High density metal-insulator-metal capacitor based on $ZrO_2/Al_2/O_3/ZrO_2$ laminate dielectric," Applied Physics Letters 93 (2008), 033511.

International Search Report and Written Opinion for related PCT/EP2006/062893, dated Sep. 27, 2007.

International Search Report and Written Opinion for related PCT/EP2007/052507, dated Oct. 31, 2007.

International Search Report and Written Opinion for related PCT/EP2009/051683, dated May 14, 2009.

International Search Report and Written Opinion for related PCT/US2015/066434, dated Apr. 12, 2016.

Niinisto, J., "Atomic layer deposition of high-k dielectrics from novel cyclopentadienyl-type precursors," Dissertation, Helsinki Univ. of Technology, Inorganic Chemistry Publication Series, Espoo 2006 No. 5, 72 pgs.

Restriction requirement dated Jan. 2, 2014 for U.S. Appl. No. 13/390,452.

\* cited by examiner

HAFNIUM-CONTAINING FILM FORMING COMPOSITIONS FOR VAPOR DEPOSITION OF HAFNIUM-CONTAINING FILMS

TECHNICAL FIELD

Disclosed are Hafnium-containing film forming compositions comprising Silicon- and Hafnium-containing precursors. Also disclosed are methods of synthesizing the disclosed compositions and using the same to deposit Hafnium-containing films on substrates via vapor deposition processes.

BACKGROUND

With the scaling down of semiconductor devices such as dynamic random access memory (DRAM), new materials with high dielectric constant are required. Indeed, in order to store a sufficient charge in a capacitor with a smaller surface area, capacitors with higher permittivity are needed. Among high-k dielectrics, Group 4 based materials, such as $HfO_2$ or $ZrO_2$, are very promising since their dielectric constant is higher than $SiO_2$ or $Al_2O_3$. However, their dielectric constant varies depending on their crystalline form (Thin Solid Films 486 (2005) 125-128).

the cubic/tetragonal crystalline phase of the $ZrO_2$ layer, which is the phase having the highest k-value, has also been stabilized by doping $ZrO_2$ with a small amount of silicon or germanium (Journal of Applied Physics, 2009, 106, 024107; Applied Physics Letters, 2011, 99, 121909).

Group 4 alkylamide precursors containing cyclopentadienyl ligand have been developed, such as the one show below (Dussarrat et al., WO2007/141059; Niinisto et al., Journal of Materials Chemistry (2008), 18(43), 5243-5247). These precursors show a higher thermal stability in comparison to the tetrakis alkylamide precursors.

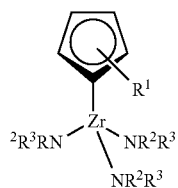

wherein $R^1$=H, Me, or Et; $R^2$&$R^3$=$C_1$-$C_4$ alkyl group.

Similar to these compounds, Group 4 precursors containing silylcyclopentadienyl ligand have been described in the literature as shown below:

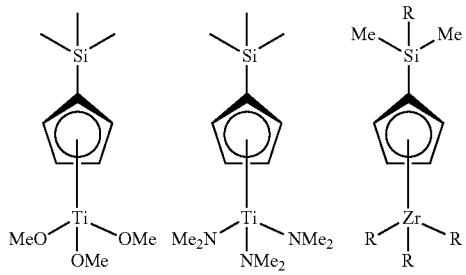

wherein R=Cl, $NMe_2$, $OSiMe_3$, $CH_2SiMe_3$, $C_6H_5$ and $CH_2Ph$ (Journal of Organometallic Chemistry, 2004, 689, 1503 for Ti methoxy compounds, JP2005/171291 to Tosoh for Ti alkylamino compounds, KR2008/0101040 to UP Chemical Co. Ltd. and Journal of Organometallic Chemistry, 1997, 547, 287 for Zr compounds).

A need remains for developing liquid or low melting point (<50° C.), highly thermally stable, with low viscosity, Hafnium precursor molecules suitable for vapor phase thin film deposition with controlled thickness and composition at high temperature.

SUMMARY

Disclosed are Hafnium-containing film forming compositions comprising Silicon- and Hafnium-containing precursors having the following formula:

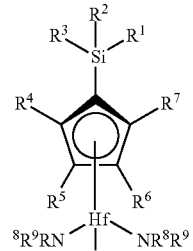

Formula I

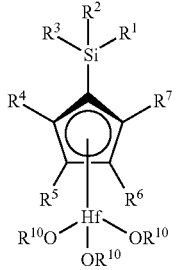

Formula II wherein each $R^1$, $R^2$, $R^3$, $R^4$, $R^5$, $R^6$, $R^7$, $R^8$, $R^9$ and $R^{10}$ is independently selected from H; a C1-C5 linear, branched, or cyclic alkyl group; or a C1-C5 linear, branched, or cyclic fluoroalkyl group. $R^1$, $R^2$ and $R^3$ may be identical or different. $R^4$, $R^5$, $R^6$ and $R^7$ may be identical or different. Each $R^8$ and $R^9$ may be identical or different. Each $R^{10}$ may be identical or different. The disclosed Hafnium-containing film forming compositions may further include one or more of the following aspects:

- $R^1$ and $R^2$ and $R^3$ being independently H, F, $CF_3$, Me, Et, nPr, iPr, nBu, iBu, sBu or tBu:
- $R^4$, $R^5$, $R^6$ and $R^7$ being independently H, F $CF_3$, Me, Et, nPr, Pr, nBu, iBu, sBu or tBu;
- $R^8$ and $R^9$ being independently H, Me, Et, nPr, iPr, nBu iBu, sBu or tBu;
- $R^{10}$ being Me, Et, nPr, iPr, nBu, iBu, sBu, or tBu;
- the Silicon- and Hafnium-containing precursor being (trimethylsilyl)cyclopentadienyl tris(Dimethylamino) Hafnium(IV) (Hf(TMS-Cp)(NMe$_2$)$_3$);
- the Silicon- and Hafnium-containing precursor being (trimethylsilyl)cyclopentadienyl tris(methylamino) Hafnium(IV) (Hf(TMS-Cp)(NHMe)$_3$);
- the Silicon- and Hafnium-containing precursor being (trimethylsilyl)cyclopentadienyl tris(Diethylamino) Hafnium(IV) (Hf(TMS-Cp)(NEt$_2$)$_3$);

the Silicon- and Hafnium-containing precursor being (trimethylsilyl)cyclopentadienyl tris(ethylamino) Hafnium(IV) (Hf(TMS-Cp)(NHEt)$_3$);

the Silicon- and Hafnium-containing precursor being (trimethylsilyl)cyclopentadienyl tris(ethylmethylamino) Hafnium(IV) (Hf(TMS-Cp)(NEtMe)$_3$);

the Silicon- and Hafnium-containing precursor being (trimethylsilyl)cyclopentadienyl tris(Di n-propylamino) Hafnium(IV) (Hf(TMS-Cp)(NnPr$_2$)$_3$);

the Silicon- and Hafnium-containing precursor being (trimethylsilyl)cyclopentadienyl tris(n-propylamino) Hafnium(IV) (Hf(TMS-Cp)(NHnPr)$_3$);

the Silicon- and Hafnium-containing precursor being (trimethylsilyl)cyclopentadienyl tris(Di isopropylamino) Hafnium(IV) (Hf(TMS-Cp)(NiPr$_2$)$_3$);

the Silicon- and Hafnium-containing precursor being (trimethylsilyl)cyclopentadienyl tris(isopropylamino) Hafnium(IV) (Hf(TMS-Cp)(NHiPr)$_3$);

the Silicon- and Hafnium-containing precursor being (trimethylsilyl)cyclopentadienyl tris(Di n-butylamino) Hafnium(IV) (Hf(TMS-Cp)(NnBu$_2$)$_3$);

the Silicon- and Hafnium-containing precursor being (trimethylsilyl)cyclopentadienyl tris(n-butylamino) Hafnium(IV) (Hf(TMS-Cp)(NHnBu)$_3$);

the Silicon- and Hafnium-containing precursor being (trimethylsilyl)cyclopentadienyl tris(Di isobutylamino) Hafnium(IV) (Hf(TMS-Cp)(NiBU$_2$)$_3$), the Silicon- and Hafnium-containing precursor being (trimethylsilyl)cyclopentadienyl tris(isobutylamino) Hafnium(IV) (Hf(TMS-Cp)(NHiBu)$_3$);

the Silicon- and Hafnium-containing precursor being (trimethylsilyl)cyclopentadienyl tris(Di sec-butylamino) Hafnium(IV) (Hf(TMS-Cp)(NsBu$_2$)$_3$);

the Silicon- and Hafnium-containing precursor being (trimethylsilyl)cyclopentadienyl tris(sec-butylamino) Hafnium(IV) (Hf(TMS-Cp)(NHsBu)$_3$);

the Silicon- and Hafnium-containing precursor being (trimethylsilyl)cyclopentadienyl tris(Di tert-butylamino) Hafnium(IV) (Hf(TMS-Cp)(NtBu$_2$)$_3$);

the Silicon- and Hafnium-containing precursor being (trimethylsilyl)cyclopentadienyl tris(tert-butylamino) Hafnium(IV) (Hf(TMS-Cp)(NHtBu)$_3$);

the Silicon- and Hafnium-containing precursor being (trimethylsilyl)cyclopentadienyl tris(methoxy) Hafnium(IV) (Hf(TMS-Cp)(OMe)$_3$);

the Silicon- and Hafnium-containing precursor being (trimethylsilyl)cyclopentadienyl tris(ethoxy) Hafnium(IV) (Hf(TMS-Cp)(OEt)$_3$);

the Silicon- and Hafnium-containing precursor being (trimethylsilyl)cyclopentadienyl tris(n-propoxy) Hafnium(IV) (Hf(TMS-Cp)(OnPr)$_3$);

the Silicon- and Hafnium-containing precursor being (trimethylsilyl)cyclopentadienyl tris(iso-propoxy) Hafnium(IV) (Hf(TMS-Cp)(OiPr)$_3$);

the Silicon- and Hafnium-containing precursor being (trimethylsilyl)cyclopentadienyl tris(tert-butoxy) Hafnium(IV) (Hf(TMS-Cp)(OtBu)$_3$);

the Silicon- and Hafnium-containing precursor being (trimethylsilyl)cyclopentadienyl tris(sec-butoxy) Hafnium(IV) (Hf(TMS-Cp)(OsBu)$_3$);

the Silicon- and Hafnium-containing precursor being (trimethylsilyl)cyclopentadienyl tris(n-butoxy) Hafnium(IV) (Hf(TMS-Cp)(OnBu)$_3$);

the Silicon- and Hafnium-containing precursor being (trimethylsilyl)cyclopentadienyl tris(iso-butoxy) Hafnium(IV) (Hf(TMS-Cp)(OiBu)$_3$);

the Silicon- and Hafnium-containing precursor being (dimethylsilyl)cyclopentadienyl tris(Dimethylamino) Hafnium(IV) (Hf(DMS-Cp)(NMe$_2$)$_3$);

the Silicon- and Hafnium-containing precursor being (dimethylsilyl)cyclopentadienyl tris(methylamino) Hafnium(IV) (Hf(DMS-Cp)(NHMe)$_3$);

the Silicon- and Hafnium-containing precursor being (dimethylsilyl)cyclopentadienyl tris(Diethylamino) Hafnium(IV) (Hf(DMS-Cp)(NEt$_2$)$_3$);

the Silicon- and Hafnium-containing precursor being (dimethylsilyl)cyclopentadienyl tris(ethylamino) Hafnium(IV) (Hf(DMS-Cp)(NHEt)$_3$);

the Silicon- and Hafnium-containing precursor being (dimethylsilyl)cyclopentadienyl tris(ethylmethylamino) Hafnium(IV) (Hf(DMS-Cp)(NEtMe)$_3$);

the Silicon- and Hafnium-containing precursor being (dimethylsilyl)cyclopentadienyl tris(Di n-propylamino) Hafnium(IV) (Hf(DMS-Cp)(NnPr$_2$)$_3$);

the Silicon- and Hafnium-containing precursor being (dimethylsilyl)cyclopentadienyl tris(n-propylamino) Hafnium(IV) (Hf(DMS-Cp)(NHnPr)$_3$);

the Silicon- and Hafnium-containing precursor being (dimethylsilyl)cyclopentadienyl tris(Di isopropylamino) Hafnium(IV) (Hf(DMS-Cp)(NiPr$_2$)$_3$);

the Silicon- and Hafnium-containing precursor being (dimethylsilyl)cyclopentadienyl tris(isopropylamino) Hafnium(IV) (Hf(DMS-Cp)(NHiPr)$_3$);

the Silicon- and Hafnium-containing precursor being (dimethylsilyl)cyclopentadienyl tris(Di n-butylamino) Hafnium(IV) (Hf(DMS-Cp)(NnBu$_2$)$_3$);

the Silicon- and Hafnium-containing precursor being (dimethylsilyl)cyclopentadienyl tris(n-butylamino) Hafnium(IV) (Hf(DMS-Cp)(NHnBu)$_3$);

the Silicon- and Hafnium-containing precursor being (dimethylsilyl)cyclopentadienyl tris(Di isobutylamino) Hafnium(IV) (Hf(DMS-Cp)(NiBu$_2$)$_3$);

the Silicon- and Hafnium-containing precursor being (dimethylsilyl)cyclopentadienyl tris(isobutylamino) Hafnium(IV) (Hf(DMS-Cp)(NHiBu)$_3$);

the Silicon- and Hafnium-containing precursor being (dimethylsilyl)cyclopentadienyl tris(Di sec-butylamino) Hafnium(IV) (Hf(DMS-Cp)(NsBU$_2$)$_3$), the Silicon- and Hafnium-containing precursor being (dimethylsilyl)cyclopentadienyl tris(sec-butylamino) Hafnium(IV) (Hf(DMS-Cp)(NHsBu)$_3$);

the Silicon- and Hafnium-containing precursor being (dimethylsilyl)cyclopentadienyl tris(Di tert-butylamino) Hafnium(IV) (Hf(DMS-Cp)(NtBu$_2$)$_3$);

the Silicon- and Hafnium-containing precursor being (dimethylsilyl)cyclopentadienyl tris(tert-butylamino) Hafnium(IV) (Hf(DMS-Cp)(NHtBu)$_3$);

the Silicon- and Hafnium-containing precursor being (dimethylsilyl)cyclopentadienyl tris(methoxy) Hafnium(IV) (Hf(DMS-Cp)(OMe)$_3$);

the Silicon- and Hafnium-containing precursor being (dimethylsilyl)cyclopentadienyl tris(ethoxy) Hafnium(IV) (Hf(DMS-Cp)(OEt)$_3$);

the Silicon- and Hafnium-containing precursor being (dimethylsilyl)cyclopentadienyl tris(n-propoxy) Hafnium(IV) (Hf(DMS-Cp)(OnPr)$_3$);

the Silicon- and Hafnium-containing precursor being (dimethylsilyl)cyclopentadienyl tris(isopropoxy) Hafnium(IV) (Hf(DMS-Cp)(OiPr)$_3$);

the Silicon- and Hafnium-containing precursor being (dimethylsilyl)cyclopentadienyl tris(tert-butoxy) Hafnium(IV) (Hf(DMS-Cp)(OtBu)$_3$);

the Silicon- and Hafnium-containing precursor being (dimethylsilyl)cyclopentadienyl tris(sec-butoxy) Hafnium (IV) (Hf(DMS-Cp)(OsBu)$_3$);

the Silicon- and Hafnium-containing precursor being (dimethylsilyl)cyclopentadienyl tris(n-butoxy) Hafnium (IV) (Hf(DMS-Cp)(OnBu)$_3$);

the Silicon- and Hafnium-containing precursor being (dimethylsilyl)cyclopentadienyl tris(isobutoxy) Hafnium (IV) (Hf(DMS-Cp)(OiBu)$_3$);

the Silicon- and Hafnium-containing precursor being (trifluorosilyl)cyclopentadienyl tris(Dimethylamino) Hafnium(IV) (Hf(F$_3$Si-Cp)(NMe$_2$)$_3$);

the Silicon- and Hafnium-containing precursor being (trifluorosilyl)cyclopentadienyl tris(methylamino) Hafnium(IV) (Hf(F$_3$Si-Cp)(NHMe)$_3$);

the Silicon- and Hafnium-containing precursor being (trifluorosilyl)cyclopentadienyl tris(Diethylamino) Hafnium(IV) (Hf(F$_3$Si-Cp)(NEt$_2$)$_3$);

the Silicon- and Hafnium-containing precursor being (trifluorosilyl)cyclopentadienyl tris(ethylamino) Hafnium (IV) (Hf(F$_3$Si-Cp)(NHEt)$_3$);

the Silicon- and Hafnium-containing precursor being (trifluorosilyl)cyclopentadienyl tris(Ethylmethylamino) Hafnium(IV) (Hf(F$_3$Si-Cp)(NEtMe)$_3$);

the Silicon- and Hafnium-containing precursor being (trifluorosilyl)cyclopentadienyl tris(Di n-propylamino) Hafnium(IV) (Hf(F$_3$Si-Cp)(NnPr$_2$)$_3$);

the Silicon- and Hafnium-containing precursor being (trifluorosilyl)cyclopentadienyl tris(n-propylamino) Hafnium(IV) (Hf(F$_3$Si-Cp)(NHnPr)$_3$);

the Silicon- and Hafnium-containing precursor being (trifluorosilyl)cyclopentadienyl tris(Di isopropylamino) Hafnium(IV) (Hf(F$_3$Si-Cp)(NiPr$_2$)$_3$);

the Silicon- and Hafnium-containing precursor being (trifluorosilyl)cyclopentadienyl tris(isopropylamino) Hafnium(IV) (Hf(F$_3$Si-Cp)(NHiPr)$_3$);

the Silicon- and Hafnium-containing precursor being (trifluorosilyl)cyclopentadienyl tris(Di n-butylamino) Hafnium(IV) (Hf(F$_3$Si-Cp)(NnBu$_2$)$_3$);

the Silicon- and Hafnium-containing precursor being (trifluorosilyl)cyclopentadienyl tris(n-butylamino) Hafnium(IV) (Hf(F$_3$Si-Cp)(NHnBu)$_3$);

the Silicon- and Hafnium-containing precursor being (trifluorosilyl)cyclopentadienyl tris(Di isobutylamino) Hafnium(IV) (Hf(F$_3$Si-Cp)(NiBu$_2$)$_3$);

the Silicon- and Hafnium-containing precursor being (trifluorosilyl)cyclopentadienyl tris(isobutylamino) Hafnium(IV) (Hf(F$_3$Si-Cp)(NHiBu)$_3$);

the Silicon- and Hafnium-containing precursor being (trifluorosilyl)cyclopentadienyl tris(Di sec-butylamino) Hafnium(IV) (Hf(F$_3$Si-Cp)(NsBu$_2$)$_3$);

the Silicon- and Hafnium-containing precursor being (trifluorosilyl)cyclopentadienyl tris(sec-butylamino) Hafnium(IV) (Hf(F$_3$Si-Cp)(NHsBu)$_3$);

the Silicon- and Hafnium-containing precursor being (trifluorosilyl)cyclopentadienyl tris(Di tert-butylamino) Hafnium(IV) (Hf(F$_3$Si-Cp)(NtBu$_2$)$_3$);

the Silicon- and Hafnium-containing precursor being (trifluorosilyl)cyclopentadienyl tris(tert-butylamino) Hafnium(IV) (Hf(F$_3$Si-Cp)(NHtBu)$_3$);

the Silicon- and Hafnium-containing precursor being (trifluorosilyl)cyclopentadienyl tris(methoxy) Hafnium (IV) (Hf(F$_3$Si-Cp)(OMe)$_3$);

the Silicon- and Hafnium-containing precursor being (trifluorosilyl)cyclopentadienyl tris(ethoxy) Hafnium(IV) (Hf(F$_3$Si-Cp)(OEt)$_3$);

the Silicon- and Hafnium-containing precursor being (trifluorosilyl)cyclopentadienyl tris(n-propoxy) Hafnium (IV) (Hf(F$_3$Si-Cp)(OnPr)$_3$);

the Silicon- and Hafnium-containing precursor being (trifluorosilyl)cyclopentadienyl tris(isopropoxy) Hafnium (IV) (Hf(F$_3$Si-Cp)(OiPr)$_3$);

the Silicon- and Hafnium-containing precursor being (trifluorosilyl)cyclopentadienyl tris(tert-butoxy) Hafnium (IV) (Hf(F$_3$Si-Cp)(OtBu)$_3$);

the Silicon- and Hafnium-containing precursor being (trifluorosilyl)cyclopentadienyl tris(sec-butoxy) Hafnium (IV) (Hf(F$_3$Si-Cp)(OsBu)$_3$);

the Silicon- and Hafnium-containing precursor being (trifluorosilyl)cyclopentadienyl tris(n-butoxy) Hafnium (IV) (Hf(F$_3$Si-Cp)(OnBu)$_3$);

the Silicon- and Hafnium-containing precursor being (trifluorosilyl)cyclopentadienyl tris(isobutoxy) Hafnium (IV) (Hf(F$_3$Si-Cp)(OiBu)$_3$);

the Silicon- and Hafnium-containing precursor being (difluorosilyl)cyclopentadienyl tris(Dimethylamino) Hafnium(IV) (Hf(F$_2$HSi-Cp)(NMe$_2$)$_3$);

the Silicon- and Hafnium-containing precursor being (difluorosilyl)cyclopentadienyl tris(methylamino) Hafnium(IV) (Hf(F$_2$HSi-Cp)(NHMe)$_3$);

the Silicon- and Hafnium-containing precursor being (difluorosilyl)cyclopentadienyl tris(Diethylamino) Hafnium(IV) (Hf(F$_2$HSi-Cp)(NEt$_2$)$_3$);

the Silicon- and Hafnium-containing precursor being (difluorosilyl)cyclopentadienyl tris(Diethylamino) Hafnium(IV) (Hf(F$_2$HSi-Cp)(NHEt)$_3$);

the Silicon- and Hafnium-containing precursor being (difluorosilyl)cyclopentadienyl tris(Ethylmethylamino) Hafnium(IV) (Hf(F$_2$HSi-Cp)(NEtMe)$_3$);

the Silicon- and Hafnium-containing precursor being (difluorosilyl)cyclopentadienyl tris(Di n-propylamino) Hafnium(IV) (Hf(F$_2$HSi-Cp)(NnPr$_2$)$_3$);

the Silicon- and Hafnium-containing precursor being (difluorosilyl)cyclopentadienyl tris(n-propylamino) Hafnium(IV) (Hf(F$_2$HSi-Cp)(NHnPr)$_3$);

the Silicon- and Hafnium-containing precursor being (difluorosilyl)cyclopentadienyl tris(Di isopropylamino) Hafnium(IV) (Hf(F$_2$HSi-Cp)(NiPr$_2$)$_3$), the Silicon- and Hafnium-containing precursor being (difluorosilyl)cyclopentadienyl tris(isopropylamino) Hafnium(IV) (Hf(F$_2$HSi-Cp)(NHiPr)$_3$);

the Silicon- and Hafnium-containing precursor being (difluorosilyl)cyclopentadienyl tris(Di n-butylamino) Hafnium(IV) (Hf(F$_2$HSi-Cp)(NnBu$_2$)$_3$);

the Silicon- and Hafnium-containing precursor being (difluorosilyl)cyclopentadienyl tris(n-butylamino) Hafnium(IV) (Hf(F$_2$HSi-Cp)(NHnBu)$_3$);

the Silicon- and Hafnium-containing precursor being (difluorosilyl)cyclopentadienyl tris(Di isobutylamino) Hafnium(IV) (Hf(F$_2$HSi-Cp)(NiBu$_2$)$_3$);

the Silicon- and Hafnium-containing precursor being (difluorosilyl)cyclopentadienyl tris(isobutylamino) Hafnium(IV) (Hf(F$_2$HSi-Cp)(NHiBu)$_3$);

the Silicon- and Hafnium-containing precursor being (difluorosilyl)cyclopentadienyl tris(Di sec-butylamino) Hafnium(IV) (Hf(F$_2$HSi-C$_P$)(NsBU$_2$)$_3$), the Silicon- and Hafnium-containing precursor being (difluorosilyl)cyclopentadienyl tris(sec-butylamino) Hafnium(IV) (Hf(F$_2$HSi-Cp)(NHsBu)$_3$);

the Silicon- and Hafnium-containing precursor being (difluorosilyl)cyclopentadienyl tris(Di tert-butylamino) Hafnium(IV) (Hf(F$_2$HSi-Cp)(NtBu$_2$)$_3$);

the Silicon- and Hafnium-containing precursor being (difluorosilyl)cyclopentadienyl tris(tert-butylamino) Hafnium(IV) (Hf(F$_2$HSi-Cp)(NHtBu)$_3$);

the Silicon- and Hafnium-containing precursor being (difluorosilyl)cyclopentadienyl tris(methoxy) Hafnium(IV) (Hf(F$_2$HSi-Cp)(OMe)$_3$);

the Silicon- and Hafnium-containing precursor being (difluorosilyl)cyclopentadienyl tris(ethoxy) Hafnium(IV) (Hf(F$_2$HSi-Cp)(OEt)$_3$);

the Silicon- and Hafnium-containing precursor being (difluorosilyl)cyclopentadienyl tris(n-propoxy) Hafnium(IV) (Hf(F$_2$HSi-Cp)(OnPr)$_3$);

the Silicon- and Hafnium-containing precursor being (difluorosilyl)cyclopentadienyl tris(isopropoxy) Hafnium(IV) (Hf(F$_2$HSi-Cp)(OiPr)$_3$);

the Silicon- and Hafnium-containing precursor being (difluorosilyl)cyclopentadienyl tris(tert-butoxy) Hafnium(IV) (Hf(F$_2$HSi-Cp)(OtBu)$_3$);

the Silicon- and Hafnium-containing precursor being (difluorosilyl)cyclopentadienyl tris(sec-butoxy) Hafnium(IV) (Hf(F$_2$HSi-Cp)(OsBu)$_3$);

the Silicon- and Hafnium-containing precursor being (difluorosilyl)cyclopentadienyl tris(n-butoxy) Hafnium(IV) (Hf(F$_2$HSi-Cp)(OnBu)$_3$);

the Silicon- and Hafnium-containing precursor being (difluorosilyl)cyclopentadienyl tris(isobutoxy) Hafnium(IV) (Hf(F$_2$HSi-Cp)(OiBu)$_3$);

the Silicon- and Hafnium-containing precursor being (monofluorosilyl)cyclopentadienyl tris(Dimethylamino) Hafnium(IV) (Hf(FH$_2$Si-Cp)(NMe$_2$)$_3$);

the Silicon- and Hafnium-containing precursor being (monofluorosilyl)cyclopentadienyl tris(methylamino) Hafnium(IV) (Hf(FH$_2$Si-Cp)(NHme)$_3$);

the Silicon- and Hafnium-containing precursor being (monofluorosilyl)cyclopentadienyl tris(Diethylamino) Hafnium(IV) (Hf(FH$_2$Si-Cp)(NEt$_2$)$_3$);

the Silicon- and Hafnium-containing precursor being (monofluorosilyl)cyclopentadienyl tris(ethylamino) Hafnium(IV) (Hf(FH$_2$Si-Cp)(NHEt)$_3$);

the Silicon- and Hafnium-containing precursor being (monofluorosilyl)cyclopentadienyl tris(Ethylmethylamino) Hafnium(IV) (Hf(FH$_2$Si-Cp)(NEtMe)$_3$), the Silicon- and Hafnium-containing precursor being (monofluorosilyl)cyclopentadienyl tris(Di n-propylamino) Hafnium(IV) (Hf(FH$_2$Si-Cp)(NnPr$_2$)$_3$);

the Silicon- and Hafnium-containing precursor being (monofluorosilyl)cyclopentadienyl tris(n-propylamino) Hafnium(IV) (Hf(FH$_2$Si-Cp)(NHnPr)$_3$);

the Silicon- and Hafnium-containing precursor being (monofluorosilyl)cyclopentadienyl tris(Di isopropylamino) Hafnium(IV) (Hf(FH$_2$Si-Cp)(NiPr$_2$)$_3$);

the Silicon- and Hafnium-containing precursor being (monofluorosilyl)cyclopentadienyl tris(isopropylamino) Hafnium(IV) (Hf(FH$_2$Si-Cp)(NHiPr)$_3$);

the Silicon- and Hafnium-containing precursor being (monofluorosilyl)cyclopentadienyl tris(Di n-butylamino) Hafnium(IV) (Hf(FH$_2$Si-Cp)(NnBu$_2$)$_3$);

the Silicon- and Hafnium-containing precursor being (monofluorosilyl)cyclopentadienyl tris(n-butylamino) Hafnium(IV) (Hf(FH$_2$Si-Cp)(NHnBU)$_3$), the Silicon- and Hafnium-containing precursor being (monofluorosilyl)cyclopentadienyl tris(Di isobutylamino) Hafnium(IV) (Hf(FH$_2$Si-Cp)(NiBu$_2$)$_3$);

the Silicon- and Hafnium-containing precursor being (monofluorosilyl)cyclopentadienyl tris(isobutylamino) Hafnium(IV) (Hf(FH$_2$Si-Cp)(NHiBu)$_3$);

the Silicon- and Hafnium-containing precursor being (monofluorosilyl)cyclopentadienyl tris(Di sec-butylamino) Hafnium(IV) (Hf(FH$_2$Si-Cp)(NsBu$_2$)$_3$);

the Silicon- and Hafnium-containing precursor being (monofluorosilyl)cyclopentadienyl tris(sec-butylamino) Hafnium(IV) (Hf(FH$_2$Si-Cp)(NHsBu)$_3$);

the Silicon- and Hafnium-containing precursor being (monofluorosilyl)cyclopentadienyl tris(Di tert-butylamino) Hafnium(IV) (Hf(FH$_2$Si-Cp)(NtBU$_2$)$_3$), the Silicon- and Hafnium-containing precursor being (monofluorosilyl)cyclopentadienyl tris(tert-butylamino) Hafnium(IV) (Hf(FH$_2$Si-Cp)(NHtBu)$_3$);

the Silicon- and Hafnium-containing precursor being (monofluorosilyl)cyclopentadienyl tris(methoxy) Hafnium(IV) (Hf(FH$_2$Si-Cp)(OMe)$_3$);

the Silicon- and Hafnium-containing precursor being (monofluorosilyl)cyclopentadienyl tris(ethoxy) Hafnium(IV) (Hf(FH$_2$Si-Cp)(OEt)$_3$);

the Silicon- and Hafnium-containing precursor being (monofluorosilyl)cyclopentadienyl tris(n-propoxy) Hafnium(IV) (Hf(FH$_2$Si-Cp)(OnPr)$_3$);

the Silicon- and Hafnium-containing precursor being (monofluorosilyl)cyclopentadienyl tris(isopropoxy) Hafnium(IV) (Hf(FH$_2$Si-Cp)(OiPr)$_3$);

the Silicon- and Hafnium-containing precursor being (monofluorosilyl)cyclopentadienyl tris(tert-butoxy) Hafnium(IV) (Hf(FH$_2$Si-Cp)(OtBU)$_3$);

the Silicon- and Hafnium-containing precursor being (monofluorosilyl)cyclopentadienyl tris(sec-butoxy) Hafnium(IV) (Hf(FH$_2$Si-Cp)(OsBu)$_3$);

the Silicon- and Hafnium-containing precursor being (monofluorosilyl)cyclopentadienyl tris(n-butoxy) Hafnium(IV) (Hf(FH$_2$Si-Cp)(OnBu)$_3$);

the Silicon- and Hafnium-containing precursor being (monofluorosilyl)cyclopentadienyl tris(isobutoxy) Hafnium(IV) (Hf(FH$_2$Si-Cp)(OiBu)$_3$);

the Silicon- and Hafnium-containing precursor being (fluoro dimethylsilyl)cyclopentadienyl tris(Dimethylamino) Hafnium(IV) (Hf(FMe$_2$Si-Cp)(NMe$_2$)$_3$);

the Silicon- and Hafnium-containing precursor being (fluoro dimethylsilyl)cyclopentadienyl tris(methylamino) Hafnium(IV) (Hf(FMe$_2$Si-Cp)(NHMe)$_3$), the Silicon- and Hafnium-containing precursor being (fluoro dimethylsilyl)cyclopentadienyl tris(Diethylamino) Hafnium(IV) (Hf(FMe$_2$Si-Cp)(NEt$_2$)$_3$);

the Silicon- and Hafnium-containing precursor being (fluoro dimethylsilyl)cyclopentadienyl tris(ethylamino) Hafnium(IV) (Hf(FMe$_2$Si-Cp)(NHEt)$_3$);

the Silicon- and Hafnium-containing precursor being (fluoro dimethylsilyl)cyclopentadienyl tris(Ethylmethylamino) Hafnium(IV) (Hf(FMe$_2$Si-Cp)(NEtMe)$_3$);

the Silicon- and Hafnium-containing precursor being (fluoro dimethylsilyl)cyclopentadienyl tris(Di n-propylamino) Hafnium(IV) (Hf(FMe$_2$Si-Cp)(NnPr$_2$)$_3$);

the Silicon- and Hafnium-containing precursor being (fluoro dimethylsilyl)cyclopentadienyl tris(n-propylamino) Hafnium(IV) (Hf(FMe$_2$Si-Cp)(NHnPr)$_3$);

the Silicon- and Hafnium-containing precursor being (fluoro dimethylsilyl)cyclopentadienyl tris(Di isopropylamino) Hafnium(IV) (Hf(FMe$_2$Si-Cp)(NiPr$_2$)$_3$);

the Silicon- and Hafnium-containing precursor being (fluoro dimethylsilyl)cyclopentadienyl tris(isopropylamino) Hafnium(IV) (Hf(FMe$_2$Si-Cp)(NHiPr)$_3$);

the Silicon- and Hafnium-containing precursor being (fluoro dimethylsilyl)cyclopentadienyl tris(Di n-butylamino) Hafnium(IV) (Hf(FMe$_2$Si-Cp)(NnBu$_2$)$_3$);

the Silicon- and Hafnium-containing precursor being (fluoro dimethylsilyl)cyclopentadienyl tris(n-butylamino) Hafnium(IV) (Hf(FMe$_2$Si-Cp)(NHnBu)$_3$);

the Silicon- and Hafnium-containing precursor being (fluoro dimethylsilyl)cyclopentadienyl tris(Di isobutylamino) Hafnium(IV) (Hf(FMe$_2$Si-Cp)(NiBu$_2$)$_3$);

the Silicon- and Hafnium-containing precursor being (fluoro dimethylsilyl)cyclopentadienyl tris(isobutylamino) Hafnium(IV) (Hf(FMe$_2$Si-Cp)(NHiBU)$_3$);

the Silicon- and Hafnium-containing precursor being (fluoro dimethylsilyl)cyclopentadienyl tris(Di sec-butylamino) Hafnium(IV) (Hf(FMe$_2$Si-Cp)(NsBu$_2$)$_3$);

the Silicon- and Hafnium-containing precursor being (fluoro dimethylsilyl)cyclopentadienyl tris(sec-butylamino) Hafnium(IV) (Hf(FMe$_2$Si-Cp)(NHsBu)$_3$);

the Silicon- and Hafnium-containing precursor being (fluoro dimethylsilyl)cyclopentadienyl tris(Di tert-butylamino) Hafnium(IV) (Hf(FMe$_2$Si-Cp)(NtBu$_2$)$_3$);

the Silicon- and Hafnium-containing precursor being (fluoro dimethylsilyl)cyclopentadienyl tris(tert-butylamino) Hafnium(IV) (Hf(FMe$_2$Si-Cp)(NHtBu)$_3$);

the Silicon- and Hafnium-containing precursor being (fluoro dimethylsilyl)cyclopentadienyl tris(methoxy) Hafnium(IV) (Hf(FMe$_2$Si-Cp)(OMe)$_3$);

the Silicon- and Hafnium-containing precursor being (fluoro dimethylsilyl)cyclopentadienyl tris(ethoxy) Hafnium(IV) (Hf(FMe$_2$Si-Cp)(OEt)$_3$);

the Silicon- and Hafnium-containing precursor being (fluoro dimethylsilyl)cyclopentadienyl tris(n-propoxy) Hafnium(IV) (Hf(FMe$_2$Si-Cp)(OnPr)$_3$);

the Silicon- and Hafnium-containing precursor being (fluoro dimethylsilyl)cyclopentadienyl tris(isopropoxy) Hafnium(IV) (Hf(FMe$_2$Si-Cp)(OiPr)$_3$);

the Silicon- and Hafnium-containing precursor being (fluoro dimethylsilyl)cyclopentadienyl tris(tert-butoxy) Hafnium(IV) (Hf(FMe$_2$Si-Cp)(OtBu)$_3$);

the Silicon- and Hafnium-containing precursor being (fluoro dimethylsilyl)cyclopentadienyl tris(sec-butoxy) Hafnium(IV) (Hf(FMe$_2$Si-Cp)(OsBu)$_3$);

the Silicon- and Hafnium-containing precursor being (fluoro dimethylsilyl)cyclopentadienyl tris(n-butoxy) Hafnium(IV) (Hf(FMe$_2$Si-Cp)(OnBu)$_3$);

the Silicon- and Hafnium-containing precursor being (fluoro dimethylsilyl)cyclopentadienyl tris(isobutoxy) Hafnium(IV) (Hf(FMe$_2$Si-Cp)(OiBu)$_3$);

the Silicon- and Hafnium-containing precursor being (tris (trifluoromethyl)silyl)cyclopentadienyl tris(Dimethylamino) Hafnium(IV) (Hf((CF$_3$)$_3$Si-Cp)(NMe$_2$)$_3$);

the Silicon- and Hafnium-containing precursor being (tris (trifluoromethyl)silyl)cyclopentadienyl tris(methylamino) Hafnium(IV) (Hf((CF$_3$)$_3$Si-Cp)(NHMe)$_3$);

the Silicon- and Hafnium-containing precursor being (tris (trifluoromethyl)silyl)cyclopentadienyl tris(Diethylamino) Hafnium(IV) (Hf((CF$_3$)$_3$Si-Cp)(NEt$_2$)$_3$);

the Silicon- and Hafnium-containing precursor being (tris (trifluoromethyl)silyl)cyclopentadienyl tris(ethylamino) Hafnium(IV) (Hf((CF$_3$)$_3$Si-Cp)(NHEt)$_3$);

the Silicon- and Hafnium-containing precursor being (tris (trifluoromethyl)silyl)cyclopentadienyl tris(Ethylmethylamino) Hafnium(IV) (Hf((CF$_3$)$_3$Si-Cp)(NEtMe)$_3$);

the Silicon- and Hafnium-containing precursor being (tris (trifluoromethyl)silyl)cyclopentadienyl tris(Di n-propylamino) Hafnium(IV) (Hf((CF$_3$)$_3$Si-Cp)(NnPr$_2$)$_3$);

the Silicon- and Hafnium-containing precursor being (tris (trifluoromethyl)silyl)cyclopentadienyl tris(n-propylamino) Hafnium(IV) (Hf((CF$_3$)$_3$Si-Cp)(NHnPr)$_3$);

the Silicon- and Hafnium-containing precursor being (tris (trifluoromethyl)silyl)cyclopentadienyl tris(Di isopropylamino) Hafnium(IV) (Hf((CF$_3$)$_3$Si-Cp)(NiPr$_2$)$_3$);

the Silicon- and Hafnium-containing precursor being (tris (trifluoromethyl)silyl)cyclopentadienyl tris(isopropylamino) Hafnium(IV) (Hf((CF$_3$)$_3$Si-Cp)(NHiPr)$_3$);

the Silicon- and Hafnium-containing precursor being (tris (trifluoromethyl)silyl)cyclopentadienyl tris(Di n-butylamino) Hafnium(IV) (Hf((CF$_3$)$_3$Si-Cp)(NnBu$_2$)$_3$);

the Silicon- and Hafnium-containing precursor being (tris (trifluoromethyl)silyl)cyclopentadienyl tris(n-butylamino) Hafnium(IV) (Hf((CF$_3$)$_3$Si-Cp)(NHnBu)$_3$);

the Silicon- and Hafnium-containing precursor being (tris (trifluoromethyl)silyl)cyclopentadienyl tris(Di isobutylamino) Hafnium(IV) (Hf((CF$_3$)$_3$Si-Cp)(NiBu$_2$)$_3$);

the Silicon- and Hafnium-containing precursor being (tris (trifluoromethyl)silyl)cyclopentadienyl tris(isobutylamino) Hafnium(IV) (Hf((CF$_3$)$_3$Si-Cp)(NHiBu)$_3$);

the Silicon- and Hafnium-containing precursor being (tris (trifluoromethyl)silyl)cyclopentadienyl tris(Di sec-butylamino) Hafnium(IV) (Hf((CF$_3$)$_3$Si-Cp)(NsBu$_2$)$_3$);

the Silicon- and Hafnium-containing precursor being (tris (trifluoromethyl)silyl)cyclopentadienyl tris(sec-butylamino) Hafnium(IV) (Hf((CF$_3$)$_3$Si-Cp)(NHsBu)$_3$);

the Silicon- and Hafnium-containing precursor being (tris (trifluoromethyl)silyl)cyclopentadienyl tris(Di tert-butylamino) Hafnium(IV) (Hf((CF$_3$)$_3$Si-Cp)(NtBu$_2$)$_3$);

the Silicon- and Hafnium-containing precursor being (tris (trifluoromethyl)silyl)cyclopentadienyl tris(tert-butylamino) Hafnium(IV) (Hf((CF$_3$)$_3$Si-Cp)(NHtBu)$_3$);

the Silicon- and Hafnium-containing precursor being (tris (trifluoromethyl)silyl)cyclopentadienyl tris(methoxy) Hafnium(IV) (Hf((CF$_3$)$_3$Si-Cp)(OMe)$_3$);

the Silicon- and Hafnium-containing precursor being (tris (trifluoromethyl)silyl)cyclopentadienyl tris(ethoxy) Hafnium(IV) (Hf((CF$_3$)$_3$Si-Cp)(OEt)$_3$);

the Silicon- and Hafnium-containing precursor being (tris (trifluoromethyl)silyl)cyclopentadienyl tris(n-propoxy) Hafnium(IV) (Hf((CF$_3$)$_3$Si-Cp)(OnPr)$_3$);

the Silicon- and Hafnium-containing precursor being (tris (trifluoromethyl)silyl)cyclopentadienyl tris(isopropoxy) Hafnium(IV) (Hf((CF$_3$)$_3$Si-Cp)(OiPr)$_3$);

the Silicon- and Hafnium-containing precursor being (tris (trifluoromethyl)silyl)cyclopentadienyl tris(tert-butoxy) Hafnium(IV) (Hf((CF$_3$)$_3$Si-Cp)(OtBu)$_3$);

the Silicon- and Hafnium-containing precursor being (tris (trifluoromethyl)silyl)cyclopentadienyl tris(sec-butoxy) Hafnium(IV) (Hf((CF$_3$)$_3$Si-Cp)(OsBu)$_3$);

the Silicon- and Hafnium-containing precursor being (tris (trifluoromethyl)silyl)cyclopentadienyl tris(n-butoxy) Hafnium(IV) (Hf((CF$_3$)$_3$Si-Cp)(OnBu)$_3$);

the Silicon- and Hafnium-containing precursor being (tris (trifluoromethyl)silyl)cyclopentadienyl tris(isobutoxy) Hafnium(IV) (Hf((CF$_3$)$_3$Si-Cp)(OiBu)$_3$);

the Silicon- and Hafnium-containing precursor being (bis (trifluoromethyl)silyl)cyclopentadienyl tris(Dimethylamino) Hafnium(IV) (Hf((CF$_3$)$_2$HSi-Cp)(NMe$_2$)$_3$);

the Silicon- and Hafnium-containing precursor being (bis (trifluoromethyl)silyl)cyclopentadienyl tris(methylamino) Hafnium(IV) (Hf((CF$_3$)$_2$HSi-Cp)(NHMe)$_3$);

the Silicon- and Hafnium-containing precursor being (bis (trifluoromethyl)silyl)cyclopentadienyl tris(Diethylamino) Hafnium(IV) (Hf((CF$_3$)$_2$HSi-Cp)(NEt$_2$)$_3$);

the Silicon- and Hafnium-containing precursor being (bis (trifluoromethyl)silyl)cyclopentadienyl tris(ethylamino) Hafnium(IV) (Hf((CF$_3$)$_2$HSi-Cp)(NHEt)$_3$);

the Silicon- and Hafnium-containing precursor being (bis(trifluoromethyl)silyl)cyclopentadienyl tris(Ethylmethylamino) Hafnium(IV) (Hf((CF$_3$)$_2$HSi-Cp)(NEtMe)$_3$);

the Silicon- and Hafnium-containing precursor being (bis(trifluoromethyl)silyl)cyclopentadienyl tris(Di n-propylamino) Hafnium(IV) (Hf((CF$_3$)$_2$HSi-Cp)(NnPr$_2$)$_3$);

the Silicon- and Hafnium-containing precursor being (bis(trifluoromethyl)silyl)cyclopentadienyl tris(n-propylamino) Hafnium(IV) (Hf((CF$_3$)$_2$HSi-Cp)(NHnPr)$_3$);

the Silicon- and Hafnium-containing precursor being (bis(trifluoromethyl)silyl)cyclopentadienyl tris(Di isopropylamino) Hafnium(IV) (Hf((CF$_3$)$_2$HSi-Cp)(NiPr$_2$)$_3$);

the Silicon- and Hafnium-containing precursor being (bis(trifluoromethyl)silyl)cyclopentadienyl tris(isopropylamino) Hafnium(IV) (Hf((CF$_3$)$_2$HSi-Cp)(NHiPr)$_3$);

the Silicon- and Hafnium-containing precursor being (bis(trifluoromethyl)silyl)cyclopentadienyl tris(Di n-butylamino) Hafnium(IV) (Hf((CF$_3$)$_2$HSi-Cp)(NnBu$_2$)$_3$);

the Silicon- and Hafnium-containing precursor being (bis(trifluoromethyl)silyl)cyclopentadienyl tris(n-butylamino) Hafnium(IV) (Hf((CF$_3$)$_2$HSi-Cp)(NHnBu)$_3$);

the Silicon- and Hafnium-containing precursor being (bis(trifluoromethyl)silyl)cyclopentadienyl tris(Di isobutylamino) Hafnium(IV) (Hf((CF$_3$)$_2$HSi-Cp)(NiBu$_2$)$_3$);

the Silicon- and Hafnium-containing precursor being (bis(trifluoromethyl)silyl)cyclopentadienyl tris(isobutylamino) Hafnium(IV) (Hf((CF$_3$)$_2$HSi-Cp)(NHiBu)$_3$);

the Silicon- and Hafnium-containing precursor being (bis(trifluoromethyl)silyl)cyclopentadienyl tris(Di sec-butylamino) Hafnium(IV) (Hf((CF$_3$)$_2$HSi-Cp)(NsBu$_2$)$_3$);

the Silicon- and Hafnium-containing precursor being (bis(trifluoromethyl)silyl)cyclopentadienyl tris(sec-butylamino) Hafnium(IV) (Hf((CF$_3$)$_2$HSi-Cp)(NHsBu)$_3$);

the Silicon- and Hafnium-containing precursor being (bis(trifluoromethyl)silyl)cyclopentadienyl tris(Di tert-butylamino) Hafnium(IV) (Hf((CF$_3$)$_2$HSi-Cp)(NtBu$_2$)$_3$);

the Silicon- and Hafnium-containing precursor being (bis(trifluoromethyl)silyl)cyclopentadienyl tris(tert-butylamino) Hafnium(IV) (Hf((CF$_3$)$_2$HSi-Cp)(NHtBu)$_3$);

the Silicon- and Hafnium-containing precursor being (bis(trifluoromethyl)silyl)cyclopentadienyl tris(methoxy) Hafnium(IV) (Hf((CF$_3$)$_2$HSi-Cp)(OMe)$_3$);

the Silicon- and Hafnium-containing precursor being (bis(trifluoromethyl)silyl)cyclopentadienyl tris(ethoxy) Hafnium(IV) (Hf((CF$_3$)$_2$HSi-Cp)(OEt)$_3$);

the Silicon- and Hafnium-containing precursor being (bis(trifluoromethyl)silyl)cyclopentadienyl tris(n-propoxy) Hafnium(IV) (Hf((CF$_3$)$_2$HSi-Cp)(OnPr)$_3$);

the Silicon- and Hafnium-containing precursor being (bis(trifluoromethyl)silyl)cyclopentadienyl tris(iso-propoxy) Hafnium(IV) (Hf((CF$_3$)$_2$HSi-Cp)(OiPr)$_3$);

the Silicon- and Hafnium-containing precursor being (bis(trifluoromethyl)silyl)cyclopentadienyl tris(tert-butoxy) Hafnium(IV) (Hf((CF$_3$)$_2$HSi-Cp)(OtBu)$_3$);

the Silicon- and Hafnium-containing precursor being (bis(trifluoromethyl)silyl)cyclopentadienyl tris(sec-butoxy) Hafnium(IV) (Hf((CF$_3$)$_2$HSi-Cp)(OsBu)$_3$);

the Silicon- and Hafnium-containing precursor being (bis(trifluoromethyl)silyl)cyclopentadienyl tris(n-butoxy) Hafnium(IV) (HMCF$_3$)$_2$HSi-Cp)(OnBU)$_3$);

the Silicon- and Hafnium-containing precursor being (bis(trifluoromethyl)silyl)cyclopentadienyl tris(iso-butoxy) Hafnium(IV) (Hf((CF$_3$)$_2$HSi-Cp)(OiBu)$_3$);

the Silicon- and Hafnium-containing precursor being ((trifluoromethyl)dimethylsilyl)cyclopentadienyl tris(Dimethylamino) Hafnium(IV) (Hf((CF$_3$)Me$_2$Si-Cp)(NMe$_2$)$_3$);

the Silicon- and Hafnium-containing precursor being ((trifluoromethyl)dimethylsilyl)cyclopentadienyl tris(methylamino) Hafnium(IV) (Hf((CF$_3$)Me$_2$Si-Cp)(NHMe)$_3$);

the Silicon- and Hafnium-containing precursor being ((trifluoromethyl)dimethylsilyl)cyclopentadienyl tris(Diethylamino) Hafnium(IV) (Hf((CF$_3$)Me$_2$Si-Cp)(NEt$_2$)$_3$);

the Silicon- and Hafnium-containing precursor being ((trifluoromethyl)dimethylsilyl)cyclopentadienyl tris(ethylamino) Hafnium(IV) (Hf((CF$_3$)Me$_2$Si-Cp)(NHEt)$_3$);

the Silicon- and Hafnium-containing precursor being ((trifluoromethyl)dimethylsilyl)cyclopentadienyl tris(Ethylmethylamino) Hafnium(IV) (Hf((CF$_3$)Me$_2$Si-Cp)(NEtMe)$_3$);

the Silicon- and Hafnium-containing precursor being ((trifluoromethyl)dimethylsilyl)cyclopentadienyl tris(Di n-propylamino) Hafnium(IV) (Hf((CF$_3$)Me$_2$Si-Cp)(NnPr$_2$)$_3$);

the Silicon- and Hafnium-containing precursor being ((trifluoromethyl)dimethylsilyl)cyclopentadienyl tris(n-propylamino) Hafnium(IV) (Hf((CF$_3$)Me$_2$Si-Cp)(NHnPr)$_3$);

the Silicon- and Hafnium-containing precursor being ((trifluoromethyl)dimethylsilyl)cyclopentadienyl tris(Di isopropylamino) Hafnium(IV) (Hf((CF$_3$)Me$_2$Si-Cp)(NiPr$_2$)$_3$);

the Silicon- and Hafnium-containing precursor being ((trifluoromethyl)dimethylsilyl)cyclopentadienyl tris(isopropylamino) Hafnium(IV) (Hf((CF$_3$)Me$_2$Si-Cp)(NHiPr)$_3$);

the Silicon- and Hafnium-containing precursor being ((trifluoromethyl)dimethylsilyl)cyclopentadienyl tris(Di n-butylamino) Hafnium(IV) (Hf((CF$_3$)Me$_2$Si-Cp)(NnBu$_2$)$_3$);

the Silicon- and Hafnium-containing precursor being ((trifluoromethyl)dimethylsilyl)cyclopentadienyl tris(n-butylamino) Hafnium(IV) (Hf((CF$_3$)Me$_2$Si-Cp)(NHnBu)$_3$);

the Silicon- and Hafnium-containing precursor being ((trifluoromethyl)dimethylsilyl)cyclopentadienyl tris(Di isobutylamino) Hafnium(IV) (Hf((CF$_3$)Me$_2$Si-Cp)(NiBu$_2$)$_3$);

the Silicon- and Hafnium-containing precursor being ((trifluoromethyl)dimethylsilyl)cyclopentadienyl tris(isobutylamino) Hafnium(IV) (Hf((CF$_3$)Me$_2$Si-Cp)(NHiBu)$_3$);

the Silicon- and Hafnium-containing precursor being ((trifluoromethyl)dimethylsilyl)cyclopentadienyl tris(Di sec-butylamino) Hafnium(IV) (Hf((CF$_3$)Me$_2$Si-Cp)(NsBu$_2$)$_3$);

the Silicon- and Hafnium-containing precursor being ((trifluoromethyl)dimethylsilyl)cyclopentadienyl tris(sec-butylamino) Hafnium(IV) (Hf((CF$_3$)Me$_2$Si-Cp)(NHsBu)$_3$);

the Silicon- and Hafnium-containing precursor being ((trifluoromethyl)dimethylsilyl)cyclopentadienyl tris(Di tert-butylamino) Hafnium(IV) (Hf((CF$_3$)Me$_2$Si-Cp)(NtBu$_2$)$_3$);

the Silicon- and Hafnium-containing precursor being ((trifluoromethyl)dimethylsilyl)cyclopentadienyl tris(tert-butylamino) Hafnium(IV) (Hf((CF$_3$)Me$_2$Si-Cp)(NHtBu)$_3$);

the Silicon- and Hafnium-containing precursor being ((trifluoromethyl)dimethylsilyl)cyclopentadienyl tris(methoxy) Hafnium(IV) (Hf((CF$_3$)Me$_2$Si-Cp)(OMe)$_3$);

the Silicon- and Hafnium-containing precursor being ((trifluoromethyl)dimethylsilyl)cyclopentadienyl tris (ethoxy) Hafnium(IV) (Hf((CF$_3$)Me$_2$Si-Cp)(OEt)$_3$);

the Silicon- and Hafnium-containing precursor being ((trifluoromethyl)dimethylsilyl)cyclopentadienyl tris (n-propoxy) Hafnium(IV) (Hf((CF$_3$)Me$_2$Si-Cp)(OnPr)$_3$);

the Silicon- and Hafnium-containing precursor being ((trifluoromethyl)dimethylsilyl)cyclopentadienyl tris (isopropoxy) Hafnium(IV) (Hf((CF$_3$)Me$_2$Si-Cp)(OiPr)$_3$);

the Silicon- and Hafnium-containing precursor being ((trifluoromethyl)dimethylsilyl)cyclopentadienyl tris (tert-butoxy) Hafnium(IV) (Hf((CF$_3$)Me$_2$Si-Cp)(OtBu)$_3$);

the Silicon- and Hafnium-containing precursor being ((trifluoromethyl)dimethylsilyl)cyclopentadienyl tris (sec-butoxy) Hafnium(IV) (Hf((CF$_3$)Me$_2$Si-Cp)(OsBu)$_3$);

the Silicon- and Hafnium-containing precursor being ((trifluoromethyl)dimethylsilyl)cyclopentadienyl tris (n-butoxy) Hafnium(IV) (Hf((CF$_3$)Me$_2$Si-Cp)(OnBu)$_3$);

the Silicon- and Hafnium-containing precursor being ((trifluoromethyl)dimethylsilyl)cyclopentadienyl tris (isobutoxy) Hafnium(IV) (Hf((CF$_3$)Me$_2$Si-Cp)(OiBu)$_3$);

the Hafnium-containing film forming composition comprising between approximately 95% w/w and approximately 100% w/w of the precursor;

the Hafnium-containing film forming composition comprising between approximately 98% w/w and approximately 100% w/w of the precursor;

the Hafnium-containing film forming composition comprising between approximately 99% w/w and approximately 100% w/w of the precursor;

the Hafnium-containing film forming composition comprising between approximately 5% w/w and approximately 50% w/w of the precursor;

the Hafnium-containing film forming composition comprising between approximately 0.0% w/w and approximately 5.0% w/w impurities;

the Hafnium-containing film forming composition comprising between approximately 0.0% w/w and approximately 2.0% w/w impurities;

the Hafnium-containing film forming composition comprising between approximately 0.0% w/w and approximately 1.0% w/w impurities;

the impurities including HfCp(OR$^{10}$)$_3$; Hf(OR$^{10}$)$_4$; HfCp(NR$_2$)$_3$, with each R independently being H, a C1-C5 linear, branched or cyclic alkyl group, or a C1-C5 linear, branched, or cyclic fluoroalkyl group; Hf(NR$_2$)$_4$, with each R independently being H, a Cl-CS linear, branched or cyclic alkyl group, or a C1-C5 linear, branched, or cyclic fluoroalkyl group; alcohol; alkylamines; dialkylamines; alkylimines; cyclopentadiene; dicyclopentadiene; (silyl)cyclopentadiene; alkylsilane; THF; ether; pentane; cyclohexane; heptanes; benzene; toluene; chlorinated metal compounds; lithium, sodium, or potassium alkylamino; lithium, sodium, or potassium alkoxy; and lithium, sodium, or potassium cyclopentadienyl;

the Hafnium-containing film forming composition comprising between approximately 0.0% w/w and approximately 2.0% w/w HfCp(OR$^{10}$)$_3$ impurities;

the Hafnium-containing film forming composition comprising between approximately 0.0% w/w and approximately 2.0% w/w Hf(OR$^{10}$)$_4$ impurities;

the Hafnium-containing film forming composition comprising between approximately 0.0% w/w and approximately 2.0% w/w HfCp(NR$_2$)$_3$ impurities, with each R independently being H, a C1-C5 linear, branched or cyclic alkyl group, or a C1-C5 linear, branched, or cyclic fluoroalkyl group;

the Hafnium-containing film forming composition comprising between approximately 0.0% w/w and approximately 2.0% w/w Hf(NR$_2$).$_4$ impurities, with each R independently being H, a Cl-CS linear, branched or cyclic alkyl group, or a C1-C5 linear, branched, or cyclic fluoroalkyl group;

the Hafnium-containing film forming composition comprising between approximately 0.0% w/w and approximately 2.0% w/w alcohol impurities;

the Hafnium-containing film forming composition comprising between approximately 0.0% w/w and approximately 2.0% w/w alkylamine impurities;

the Hafnium-containing film forming composition comprising between approximately 0.0% w/w and approximately 2.0% w/w alkylimine impurities;

the Hafnium-containing film forming composition comprising between approximately 0.0% w/w and approximately 2.0% w/w cyclopentadiene impurities;

the Hafnium-containing film forming composition comprising between approximately 0.0% w/w and approximately 2.0% w/w dicyclopentadiene impurities;

the Hafnium-containing film forming composition comprising between approximately 0.0% w/w and approximately 2.0% w/w (silyl)cyclopentadiene impurities;

the Hafnium-containing film forming composition comprising between approximately 0.0% w/w and approximately 2.0% w/w alkylsilane impurities;

the Hafnium-containing film forming composition comprising between approximately 0.0% w/w and approximately 2.0% w/w THF impurities;

the Hafnium-containing film forming composition comprising between approximately 0.0% w/w and approximately 2.0% w/w ether impurities;

the Hafnium-containing film forming composition comprising between approximately 0.0% w/w and approximately 2.0% w/w pentane impurities;

the Hafnium-containing film forming composition comprising between approximately 0.0% w/w and approximately 2.0% w/w cyclohexane impurities;

the Hafnium-containing film forming composition comprising between approximately 0.0% w/w and approximately 2.0% w/w heptanes impurities;

the Hafnium-containing film forming composition comprising between approximately 0.0% w/w and approximately 2.0% w/w benzene impurities;

the Hafnium-containing film forming composition comprising between approximately 0.0% w/w and approximately 2.0% w/w toluene impurities;

the Hafnium-containing film forming composition comprising between approximately 0.0% w/w and approximately 2.0% w/w chlorinated metal compound impurities;

the Hafnium-containing film forming composition comprising between approximately 0.0% w/w and approximately 2.0% w/w lithium, sodium, or potassium alkylamino impurities;

the Hafnium-containing film forming composition comprising between approximately 0.0% w/w and approximately 2.0% w/w lithium, sodium, or potassium alkoxy impurities;

the Hafnium-containing film forming composition comprising between approximately 0.0% w/w and approximately 2.0% w/w lithium, sodium, or potassium cyclopentadienyl impurities;

the Hafnium-containing film forming composition comprising between approximately 0 ppbw and approximately 1 ppmw metal impurities;

the Hafnium-containing film forming composition comprising between approximately 0 ppbw and approximately 500 ppbw metal impurities;

the metal impurities including Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), and Zinc (Zn);

the Hafnium-containing film forming composition comprising between approximately 0 ppbw and approximately 500 ppbw Al impurities;

the Hafnium-containing film forming composition comprising between approximately 0 ppbw and approximately 500 ppbw As impurities;

the Hafnium-containing film forming composition comprising between approximately 0 ppbw and approximately 500 ppbw Ba impurities;

the Hafnium-containing film forming composition comprising between approximately 0 ppbw and approximately 500 ppbw Be impurities;

the Hafnium-containing film forming composition comprising between approximately 0 ppbw and approximately 500 ppbw Bi impurities;

the Hafnium-containing film forming composition comprising between approximately 0 ppbw and approximately 500 ppbw Cd impurities;

the Hafnium-containing film forming composition comprising between approximately 0 ppbw and approximately 500 ppbw Ca impurities;

the Hafnium-containing film forming composition comprising between approximately 0 ppbw and approximately 500 ppbw Cr impurities;

the Hafnium-containing film forming composition comprising between approximately 0 ppbw and approximately 500 ppbw Co impurities;

the Hafnium-containing film forming composition comprising between approximately 0 ppbw and approximately 500 ppbw Cu impurities;

the Hafnium-containing film forming composition comprising between approximately 0 ppbw and approximately 500 ppbw Ga impurities;

the Hafnium-containing film forming composition comprising between approximately 0 ppbw and approximately 500 ppbw Ge impurities;

the Hafnium-containing film forming composition comprising between approximately 0 ppbw and approximately 500 ppbw Hf impurities;

the Hafnium-containing film forming composition comprising between approximately 0 ppbw and approximately 500 ppbw Zr impurities;

the Hafnium-containing film forming composition comprising between approximately 0 ppbw and approximately 500 ppbw In impurities;

the Hafnium-containing film forming composition comprising between approximately 0 ppbw and approximately 500 ppbw Fe impurities;

the Hafnium-containing film forming composition comprising between approximately 0 ppbw and approximately 500 ppbw Pb impurities;

the Hafnium-containing film forming composition comprising between approximately 0 ppbw and approximately 500 ppbw Li impurities;

the Hafnium-containing film forming composition comprising between approximately 0 ppbw and approximately 500 ppbw Mg impurities;

the Hafnium-containing film forming composition comprising between approximately 0 ppbw and approximately 500 ppbw Mn impurities;

the Hafnium-containing film forming composition comprising between approximately 0 ppbw and approximately 500 ppbw W impurities;

the Hafnium-containing film forming composition comprising between approximately 0 ppbw and approximately 500 ppbw Ni impurities;

the Hafnium-containing film forming composition comprising between approximately 0 ppbw and approximately 500 ppbw K impurities;

the Hafnium-containing film forming composition comprising between approximately 0 ppbw and approximately 500 ppbw Na impurities;

the Hafnium-containing film forming composition comprising between approximately 0 ppbw and approximately 500 ppbw Sr impurities;

the Hafnium-containing film forming composition comprising between approximately 0 ppbw and approximately 500 ppbw Th impurities;

the Hafnium-containing film forming composition comprising between approximately 0 ppbw and approximately 500 ppbw Sn impurities;

the Hafnium-containing film forming composition comprising between approximately 0 ppbw and approximately 500 ppbw Ti impurities;

the Hafnium-containing film forming composition comprising between approximately 0 ppbw and approximately 500 ppbw U impurities; and the Hafnium-containing film forming composition comprising between approximately 0 ppbw and approximately 500 ppbw Zn impurities.

Also disclosed is a Hafnium-containing film forming composition delivery device comprising a canister having an inlet conduit and an outlet conduit and containing any of the Hafnium-containing film forming compositions disclosed above. The disclosed device may include one or more of the following aspects:

the Hafnium-containing film forming composition having a total concentration of metal contaminants of less than 10 ppmw;

an end of the inlet conduit end located above a surface of the Hafnium-containing film forming composition and an end of the outlet conduit located below the surface of the Hafnium-containing film forming composition;

an end of the inlet conduit end located below a surface of the Hafnium-containing film forming composition and an end of the outlet conduit located above the surface of the Hafnium-containing film forming composition; and further comprising a diaphragm valve on the inlet and the outlet.

Also disclosed are processes for the deposition of Hafnium-containing films on substrates. The Hafnium-containing film forming compositions disclosed above are introduced into a reactor having a substrate disposed therein. At least part of the precursor is deposited onto the substrate to form the Hafnium-containing film. The disclosed processes may further include one or more of the following aspects:

- introducing a reactant into the reactor;
- the reactant being plasma-treated;
- the reactant being remote plasma-treated;
- the reactant not being plasma-treated;
- the reactant being selected from the group consisting of $H_2$, $H_2CO$, $N_2H_4$, $NH_3$, $SiH_4$, $Si_2H_6$, $Si_3H_8$, $SiH_2Me_2$, $SiH_2Et_2$, $N(SiH_3)_3$, hydrogen radicals thereof, and mixtures thereof;
- the reactant being $H_2$;
- the reactant being $NH_3$;
- the reactant being selected from the group consisting of $O_2$, $O_3$, $H_2O$, $H_2O_2$, NO, $N_2O$, $NO_2$, oxygen radicals thereof, and mixtures thereof;
- the reactant being $O_3$, $^1\Delta_g$ singlet oxygen, $^1\Sigma_g^+$ singlet oxygen, $^3\Sigma_g^-$ triplet oxygen, or combinations thereof;
- the reactant being $H_2O$;
- the reactant being plasma treated $O_2$;
- the reactant being $O_3$;
- the reactant being a Hafnium-containing precursor;
- the Hafnium-containing precursor being selected from the group consisting of $HfCp(NMe_2)_3$, $Hf(MeCp)(NMe_2)_3$, $Hf(EtCp)(NMe_2)_3$, $Hf(iPrCp)(NMe_2)_3$, $Hf(tBuCp)(NMe_2)_3$, $Hf(Cp)(NMeEt)_3$;
- the Hafnium-containing precursor being $HfCp(NMe_2)_3$;
- mixing the Hafnium-containing film forming composition and the Hafnium-containing precursor to form a mixture prior to introduction into the reactor;
- the Hafnium-containing film forming composition and the reactant being introduced into the reactor simultaneously;
- the reactor being configured for chemical vapor deposition;
- the reactor being configured for plasma enhanced chemical vapor deposition;
- the Hafnium-containing film forming composition and the reactant being introduced into the chamber sequentially;
- the reactor being configured for atomic layer deposition;
- the reactor being configured for plasma enhanced atomic layer deposition;
- the reactor being configured for spatial atomic layer deposition;
- the Hafnium-containing film being a pure Hafnium thin film;
- the pure Hafnium film having a Hf concentration between approximately 95 atomic % to approximately 100 atomic %;
- the Hafnium-containing film being a Hafnium silicide ($Hf_kSi_l$, wherein each of k and l is an integer which inclusively range from 1 to 6);
- the Hafnium silicide being $HfSi_2$;
- the Hafnium-containing film being a Hafnium oxide ($Hf_mO_n$, wherein each of m and n is an integer which inclusively range from 1 to 6);
- the Hafnium oxide being $HfO_2$;
- the hafnium oxide being in its amorphous crystalline phase;
- the hafnium oxide being in its cubic/tetragonal crystalline phase;
- the hafnium oxide film having a thickness between approximately 10 nm and approximately 50 nm;
- the hafnium oxide film having a thickness between approximately 15 nm and approximately 30 nm;
- the Hafnium-containing film being a Silicon-doped Hafnium oxide ($Hf_oSi_pO_q$), wherein and each of o and p is a decimal which inclusively range from 0 to 1 and q is an integer which inclusively range from 1 to 6;
- the silicon-doped Hafnium oxide being $Hf_{(0.99-0.5)}Si_{(0.5-0.01)}O_2$;
- the silicon-doped Hafnium oxide being $Hf_{(0.99\ to\ 0.9)}Si_{(0.1\ to\ 0.01)}O_2$;
- the silicon-doped Hafnium oxide being $Hf_{(0.95\ to\ 0.99)}Si_{(0.05\ to\ 0.01)}O_2$;
- the Hafnium-containing film being a Hafnium nitride ($Hf_qN_r$, wherein each of q and r is an integer which inclusively range from 1 to 6); and
- the Hafnium nitride being HfN.

Notation and Nomenclature

Certain abbreviations, symbols, and terms are used throughout the following description and claims, and include:

As used herein, the indefinite article "a" or "an" means one or more.

As used herein, the terms "approximately" or "about" or "ca." (from the Latin "circa") mean ±10% of the value stated.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $Hf(TMSCp)(NR^1R^2)_3$, the three $R^1$ groups may, but need not be identical to each other or to $R^2$.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation "Me" refers to a methyl group; the abbreviation "Et" refers to an ethyl group; the abbreviation "Pr" refers to a propyl group; the abbreviation "nPr" refers to a "normal" or linear propyl group; the abbreviation "iPr" refers to an isopropyl group; the abbreviation "Bu" refers to a butyl group; the abbreviation "nBu" refers to a "normal" or linear butyl group; the abbreviation "tBu" refers to a tert-butyl group, also known as 1,1-dimethylethyl; the abbreviation "sBu" refers to a sec-butyl group, also known as 1-methylpropyl; the abbreviation "iBu" refers to an iso-butyl group, also known as 2-methylpropyl; the abbreviation "amyl" refers to an amyl or pentyl group; the abbreviation "tAmyl" refers to a tert-amyl group, also known as 1,1-dimethylpropyl; the abbreviation "Cp" refers to cyclopentadienyl; the abbreviation "Cp*" refers to pentamethylcyclopentadienyl; the abbreviation "op" refers to (open)pentadienyl; the abbreviation "TMSCp" refers to the ligand (trimethylsilyl)cyclopentadienyl [$Me_3SiCp$]; the abbreviation "TMSCpH" refers to the molecule (trimethylsilyl)cyclopentadiene [Me₃SiCpH]; and the abbreviation "DMSCp" refers to the ligand (dimethylsilyl)cyclopentadienyl [Me₂SiHCp].

Please note that the films or layers deposited, such as Hafnium oxide, are listed throughout the specification and claims without reference to their proper stoichoimetry (i.e., $HfO_2$). The layers may include pure (Hf) layers, carbide ($Hf_oC_p$) layers, nitride ($Hf_kN_l$) layers, oxide ($Hf_nO_m$) layers, or mixtures thereof, wherein k, I, m, n, o, and p inclusively range from 1 to 6. For instance, Hafnium oxide is $Hf_kO_l$, where k and 1 each range from 0.5 to 5. More preferably Hafnium oxide is $HfO_2$. The oxide layer may be a mixture of different binary or ternary oxides layers. For example, the oxide layer may be $BaHfO_x$, $HfZrO_x$, $HfYO_x$, $HfAlO_x$, $HfErO_x$, $HfLaO_x$, $HfDyO_x$, wherein x ranges from 1 to 6. The oxide layer may be a stack of different oxides layers, such as for example $HfO_2/Al_2O_3$ nanolaminates. Any referenced layers may also include a Silicon oxide layer, $Si_3O_m$, wherein n ranges from 0.5 to 1.5 and m ranges from 1.5 to 3.5. More preferably, the silicon oxide layer is $SiO_2$ or $SiO_3$. The silicon oxide layer may be a silicon oxide based dielectric material, such as organic based or silicon oxide based low-k dielectric materials such as the Black Diamond II or III material by Applied Materials, Inc. Alternatively, any referenced silicon-containing layer may be pure silicon. Any silicon-containing layers may also include dopants, such as B, C, P, As and/or Ge.

The standard abbreviations of the elements from the periodic table of elements are used herein. It should be understood that elements may be referred to by these abbreviations (e.g., Mn refers to manganese, Si refers to silicon, C refers to carbon, etc.).

BRIEF DESCRIPTION OF THE FIGURES

For a further understanding of the nature and objects of the present invention, reference should be made to the following detailed description, taken in conjunction with the accompanying figure wherein.

DESCRIPTION OF PREFERRED EMBODIMENTS

Figure 1:
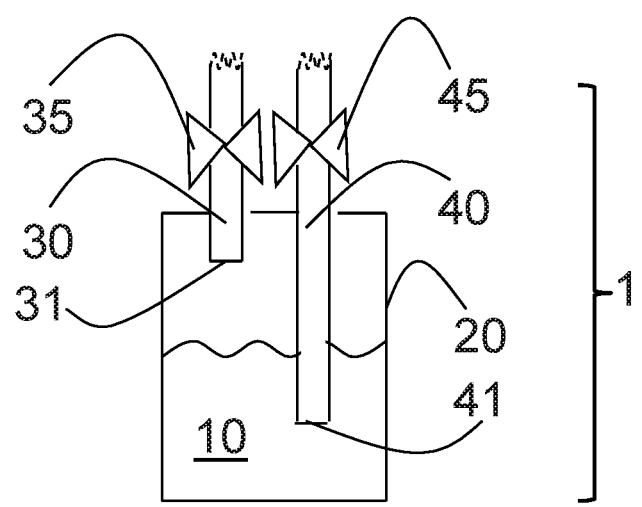
FIG. 1 is a side view of one embodiment of the Hafnium-containing film forming composition delivery device disclosed herein.

Disclosed are Hafnium-containing film forming compositions comprising a Silicon- and Hafnium-containing precursor having the following formula:

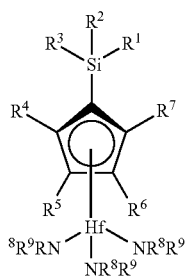

Formula I

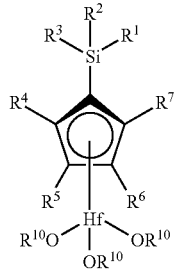

Formula II wherein each $R^1$, $R^2$, $R^3$, $R^4$, $R^5$, $R^6$, $R^7$, $R^8$, $R^9$ and $R^{10}$ is independently selected from H; a C1-05 linear, branched, or cyclic alkyl group; or a C1-C5 linear, branched, or cyclic fluoroalkyl group. $R^1$, $R^2$ and $R^3$ may be identical or different.

$R^4$, $R^5$, $R^6$ and $R^7$ may be identical or different. Each $R^8$ and $R^9$ may be identical or different. Each $R^{10}$ may be identical or different, Preferably $R^1$, $R^2$, $R^3$, $R^4$, $R^5$, $R^6$ and $R^7$ are H or Me because smaller alkyl groups may increase the volatility and decrease the melting point of the silicon- and Hafnium-containing precursor. Preferably $R^8$ and $R^9$ are H, Me or Et because smaller alkyl groups may increase the volatility and decrease the melting point of the silicon- and Hafnium-containing precursor. Preferably $R^{10}$ is Me, Et, iPr or tBu because the smaller alkyl groups (Me, Et) may increase the volatility and the larger alkyl groups (iPr, tBu) may decrease the melting point of the silicon- and Hafnium-containing precursor.

Exemplary Silicon- and Hafnium-containing precursors of Formula I include but are not limited to Hf(TMS-Cp)(NMe₂)₃, Hf(TMS-Cp)(NHMe)₃, Hf(TMS-Cp)(NEt₂)₃, Hf(TMS-Cp)(NHEt)₃, Hf(TMS-Cp)(NEtMe)₃), Hf(TMS-Cp)(NnPr₂)₃, Hf(TMS-Cp)(NHnPr)₃, Hf(TMS-Cp)(NiPr₂)₃, Hf(TMS-Cp)(NHiPr)₃, Hf(TMS-Cp)(NnBu₂)₃), Hf(TMS-Cp)(NHnBu)₃, Hf(TMS-Cp)(NiBu₂)₃, Hf(TMS-Cp)(NHiBu)₃, Hf(TMS-Cp)(NsBu₂)₃, Hf(TMS-Cp)(NHsBu)₃, Hf(TMS-Cp)(NtBu₂)₃, Hf(TMS-Cp)(NHtBu)₃, Hf(DMS-Cp)(NMe₂)₃, Hf(DMS-Cp)(NHMe)₃, Hf(DMS-Cp)(NEt₂)₃, Hf(DMS-Cp)(NHEt)₃, Hf(DMS-Cp)(NEtMe)₃, Hf(DMS-Cp)(NnPr₂)₃, Hf(DMS-Cp)(NHnPr)₃, Hf(DMS-Cp)(NiPr₂)₃, Hf(DMS-Cp)(NHiPr)₃, Hf(DMS-Cp)(NnBu₂)₃, Hf(DMS-Cp)(NHnBu)₃, Hf(DMS-Cp)(NiBu₂)₃, Hf(DMS-Cp)(NHiBu)₃, Hf(DMS-Cp)(NsBu₂)₃, Hf(DMS-Cp)(NHsBu)₃, Hf(DMS-Cp)(NtBu₂)₃, Hf(DMS-Cp)(NHtBu)₃, Hf(F₃Si-Cp)(NMe₂)₃, Hf(F₃Si-Cp)(NHMe)₃, Hf(F₃Si-Cp)(NEt₂)₃, Hf(F₃Si-Cp)(NHEt)₃, Hf(F₃Si-Cp)(NEtMe)₃, Hf(F₃Si-Cp)(NnPr₂)₃, Hf(F₃Si-Cp)(NHnPr)₃, Hf(F₃Si-Cp)(NiPr₂)₃, Hf(F₃Si-Cp)(NHiPr)₃, Hf(F₃Si-Cp)(NnBu₂)₃, Hf(F₃Si-Cp)(NHnBu)₃, Hf(F₃Si-Cp)(NiBu₂)₃, Hf(F₃Si-Cp)(NHiBu)₃, Hf(F₃Si-Cp)(NsBu₂)₃, Hf(F₃Si-Cp)(NHsBu)₃, Hf(F₃Si-Cp)(NtBu₂)₃, Hf(F₃Si-Cp)(NHtBu)₃, Hf(F₂HSi-Cp)(NMe₂)₃, Hf(F₂HSi-Cp)(NHMe)₃, Hf(F₂HSi-Cp)(NEt₂)₃, Hf(F₂HSi-Cp)(NHEt)₃, Hf(F₂HSi-Cp)(NEtMe)₃, Hf(F₂HSi-Cp)(NnPr₂)₃, Hf(F₂HSi-Cp)(NHnPr)₃, Hf(F₂HSi-Cp)(NiPr₂)₃, Hf(F₂HSi-Cp)(NHiPr)₃, Hf(F₂HSi-Cp)(NnBu₂)₃, Hf(F₂HSi-Cp)(NHnBu)₃, Hf(F₂HSi-Cp)(NiBu₂)₃, Hf(F₂HSi-Cp)(NHiBu)₃, Hf(F₂HSi-Cp)(NsBu₂)₃, Hf(F₂HSi-Cp)(NHsBu)₃, Hf(F₂HSi-Cp)(NtBu₂)₃, Hf(F₂HSi-Cp)(NHtBu)₃, Hf(FH₂Si-Cp)(NMe₂)₃, Hf(FH₂Si-Cp)(NHMe)₃, Hf(FH₂Si-Cp)(NEt₂)₃, Hf(FH₂Si-Cp)(NHEt)₃, Hf(FH₂Si-Cp)(NEtMe)₃, Hf(FH₂Si-Cp)(NnPr₂)₃, Hf(FH₂Si-Cp)(NHnPr)₃, Hf(FH₂Si-Cp)(NiPr₂)₃, Hf(FH₂Si- Cp)(NHiPr)$_3$, Hf(FH$_2$Si-Cp)(NnBu$_2$)$_3$, Hf(FH$_2$Si-Cp)(NHnBu)$_3$, Hf(FH$_2$Si-Cp)(NiBu$_2$)$_3$, Hf(FH$_2$Si-Cp)(NHiBu)$_3$, Hf(FH$_2$Si-Cp)(NsBu$_2$)$_3$, Hf(FH$_2$Si-Cp)(NHsBu)$_3$, Hf(FH$_2$Si-Cp)(NtBu$_2$)$_3$, Hf(FH$_2$Si-Cp)(NHtBu)$_3$, Hf(FMe$_2$Si-Cp)(NMe$_2$)$_3$, Hf(FMe$_2$Si-Cp)(NHMe)$_3$, Hf(FMe$_2$Si-Cp)(NEt$_2$)$_3$, Hf(FMe$_2$Si-Cp)(NHEt)$_3$, Hf(FMe$_2$Si-Cp)(NEtMe)$_3$, Hf(FMe$_2$Si-Cp)(NnPr$_2$)$_3$, Hf(FMe$_2$Si-Cp)(NHnPr)$_3$, Hf(FMe$_2$Si-Cp)(NiPr$_2$)$_3$, Hf(FMe$_2$Si-Cp)(NHiPr)$_3$, Hf(FMe$_2$Si-Cp)(NnBu$_2$)$_3$, Hf(FMe$_2$Si-Cp)(NHnBu)$_3$, Hf(FMe$_2$Si-Cp)(NiBu$_2$)$_3$, Hf(FMe$_2$Si-Cp)(NHiBu)$_3$, Hf(FMe$_2$Si-Cp)(NsBu$_2$)$_3$, Hf(FMe$_2$Si-Cp)(NHsBu)$_3$, Hf(FMe$_2$Si-Cp)(NtBu$_2$)$_3$, Hf(FMe$_2$Si-Cp)(NHtBu)$_3$, Hf((CF$_3$)$_3$Si-Cp) (NMe$_2$)$_3$, Hf((CF$_3$)$_3$Si-Cp)(NHMe)$_3$, Hf((CF$_3$)$_3$Si-Cp) (NEt$_2$)$_3$, Hf((CF$_3$)$_3$Si-Cp)(NHEt)$_3$, Hf((CF$_3$)$_3$Si-Cp) (NEtMe)$_3$, Hf((CF$_3$)$_3$Si-Cp)(NnPr$_2$)$_3$, Hf((CF$_3$)$_3$Si-Cp) (NHnPr)$_3$, Hf((CF$_3$)$_3$Si-Cp)(NiPr$_2$)$_3$, Hf((CF$_3$)$_3$Si-Cp) (NHiPr)$_3$, Hf((CF$_3$)$_3$Si-Cp)(NnBu$_2$)$_3$, Hf((CF$_3$)$_3$Si-Cp) (NHnBu)$_3$, Hf((CF$_3$)$_3$Si-Cp)(NiBu$_2$)$_3$, Hf((CF$_3$)$_3$Si-Cp) (NHiBu)$_3$, Hf((CF$_3$)$_3$Si-Cp)(NsBu$_2$)$_3$, Hf((CF$_3$)$_3$Si-Cp) (NHsBu)$_3$, Hf((CF$_3$)$_3$Si-Cp)(NtBu$_2$)$_3$, Hf((CF$_3$)$_3$Si-Cp) (NHtBu)$_3$, Hf((CF$_3$)$_2$HSi-Cp)(NMe$_2$)$_3$, Hf((CF$_3$)$_2$HSi-Cp) (NHMe)$_3$, Hf((CF$_3$)$_2$HSi-Cp)(NEt$_2$)$_3$, Hf((CF$_3$)$_2$HSi-Cp) (NHEt)$_3$, Hf((CF$_3$)$_2$HSi-Cp)(NEtMe)$_3$, Hf((CF$_3$)$_2$HSi-Cp) (NnPr$_2$)$_3$, Hf((CF$_3$)$_2$HSi-Cp)(NHnPr)$_3$, Hf((CF$_3$)$_2$HSi-Cp) (NiPr$_2$)$_3$, Hf((CF$_3$)$_2$HSi-Cp)(NHiPr)$_3$, Hf((CF$_3$)$_2$HSi-Cp) (NnBu$_2$)$_3$, Hf((CF$_3$)$_2$HSi-Cp)(NHnBu)$_3$, Hf((CF$_3$)$_2$HSi-Cp) (NiBu$_2$)$_3$, Hf((CF$_3$)$_2$HSi-Cp)(NHiBu)$_3$, Hf((CF$_3$)$_2$HSi-Cp) (NsBu$_2$)$_3$, Hf((CF$_3$)$_2$HSi-Cp)(NHsBu)$_3$, Hf((CF$_3$)$_2$HSi-Cp) (NtBu$_2$)$_3$, Hf((CF$_3$)$_2$HSi-Cp)(NHtBu)$_3$, Hf((CF$_3$)Me$_2$Si-Cp) (NMe$_2$)$_3$, Hf((CF$_3$)Me$_2$Si-Cp)(NHMe)$_3$, Hf((CF$_3$)Me$_2$Si-Cp)(NEt$_2$)$_3$, Hf((CF$_3$)Me$_2$Si-Cp)(NHEt)$_3$, Hf((CF$_3$)Me$_2$Si-Cp)(NEtMe)$_3$, Hf((CF$_3$)Me$_2$Si-Cp)(NnPr$_2$)$_3$, Hf((CF$_3$)Me$_2$Si-Cp)(NHnPr)$_3$, Hf((CF$_3$)Me$_2$Si-Cp)(NiPr$_2$)$_3$, Hf((CF$_3$)Me$_2$Si-Cp)(NHiPr)$_3$, Hf((CF$_3$)Me$_2$Si-Cp) (NnBu$_2$)$_3$, Hf((CF$_3$)Me$_2$Si-Cp)(NHnBu)$_3$, Hf((CF$_3$)Me$_2$Si-Cp)(NiBu$_2$)$_3$, Hf((CF$_3$)Me$_2$Si-Cp)(NHiBu)$_3$, Hf((CF$_3$)Me$_2$Si-Cp)(NsBu$_2$)$_3$, Hf((CF$_3$)Me$_2$Si-Cp)(NHsBu)$_3$, Hf((CF$_3$)Me$_2$Si-Cp)(NtBu$_2$)$_3$, or Hf((CF$_3$)Me$_2$Si-Cp) (NHtBu)$_3$.

Exemplary Silicon- and Hafnium-containing precursors of Formula II include but are not limited to Hf(TMS-Cp) (OMe)$_3$, Hf(TMS-Cp)(OEt)$_3$, Hf(TMS-Cp)(OnPr)$_3$, Hf(TMS-Cp)(OiPr)$_3$, Hf(TMS-Cp)(OtBu)$_3$, Hf(TMS-Cp) (OsBu)$_3$, Hf(TMS-Cp)(OnBu)$_3$, Hf(TMS-Cp)(OiBu)$_3$, Hf(DMS-Cp)(OMe)$_3$, Hf(DMS-Cp)(OEt)$_3$, Hf(DMS-Cp) (OnPr)$_3$, Hf(DMS-Cp)(OiPr)$_3$, Hf(DMS-Cp)(OtBu)$_3$, Hf(DMS-Cp)(OsBu)$_3$, Hf(DMS-Cp)(OnBu)$_3$, Hf(DMS-Cp) (OiBu)$_3$, Hf(F$_3$Si-Cp)(OMe)$_3$, Hf(F$_3$Si-Cp)(OEt)$_3$, Hf(F$_3$Si-Cp)(OnPr)$_3$, Hf(F$_3$Si-Cp)(OiPr)$_3$, Hf(F$_3$Si-Cp)(OtBu)$_3$, Hf(F$_3$Si-Cp)(OsBu)$_3$,Hf(F$_3$Si-Cp)(OnBu)$_3$, Hf(F$_3$Si-Cp) (OiBu)$_3$, Hf(F$_2$HSi-Cp)(OMe)$_3$, Hf(F$_2$HSi-Cp)(OEt)$_3$, Hf(F$_2$HSi-Cp)(OnPr)$_3$, Hf(F$_2$HSi-Cp)(OiPr)$_3$, Hf(F$_2$HSi-Cp)(OtBu)$_3$, Hf(F$_2$HSi-Cp)(OsBu)$_3$, Hf(F$_2$HSi-Cp) (OnBu)$_3$, Hf(F$_2$HSi-Cp)(OiBu)$_3$, Hf(FH$_2$Si-Cp)(OMe)$_3$, Hf(FH$_2$Si-Cp)(OEt)$_3$, Hf(FH$_2$Si-Cp)(OnPr)$_3$, Hf(FH$_2$Si-Cp) (OiPr)$_3$, Hf(FH$_2$Si-Cp)(OtBu)$_3$, Hf(FH$_2$Si-Cp)(OsBu)$_3$, Hf(FH$_2$Si-Cp)(OnBu)$_3$, Hf(FH$_2$Si-Cp)(OiBu)$_3$, Hf(FMe$_2$Si-Cp)(OMe)$_3$, Hf(FMe$_2$Si-Cp)(OEt)$_3$, Hf(FMe$_2$Si-Cp) (OnPr)$_3$, Hf(FMe$_2$Si-Cp)(OiPr)$_3$, Hf(FMe$_2$Si-Cp)(OtBu)$_3$, Hf(FMe$_2$Si-Cp)(OsBu)$_3$, Hf(FMe$_2$Si-Cp)(OnBu)$_3$, Hf(FMe$_2$Si-Cp)(OiBu)$_3$, Hf((CF$_3$)$_3$Si-Cp)(OMe)$_3$, Hf((CF$_3$)$_3$Si-Cp)(OEt)$_3$, Hf((CF$_3$)$_3$Si-Cp)(OnPr)$_3$, Hf((CF$_3$)$_3$Si-Cp)(OiPr)$_3$, Hf((CF$_3$)$_3$Si-Cp)(OtBu)$_3$, Hf((CF$_3$)$_3$Si-Cp)(OsBu)$_3$, Hf((CF$_3$)$_3$Si-Cp)(OnBu)$_3$, Hf((CF$_3$)$_3$Si-Cp)(OiBu)$_3$, Hf((CF$_3$)$_2$HSi-Cp)(OMe)$_3$, Hf((CF$_3$)$_2$HSi-Cp)(OEt)$_3$, Hf((CF$_3$)$_2$HSi-Cp)(OnPr)$_3$, Hf((CF$_3$)$_2$HSi-Cp)(OiPr)$_3$, Hf((CF$_3$)$_2$HSi-Cp)(OtBu)$_3$, Hf((CF$_3$)$_2$HSi-Cp)(OsBu)$_3$, Hf((CF$_3$)$_2$HSi-Cp)(OnBu)$_3$, Hf((CF$_3$)$_2$HSi-Cp)(OiBu)$_3$, Hf((CF$_3$)Me$_2$Si-Cp)(OMe)$_3$, Hf((CF$_3$)Me$_2$Si-Cp)(OEt)$_3$, Hf((CF$_3$)Me$_2$Si-Cp)(OnPr)$_3$, Hf((CF$_3$)Me$_2$Si-Cp)(OiPr)$_3$, Hf((CF$_3$)Me$_2$Si-Cp)(OtBu)$_3$, Hf((CF$_3$)Me$_2$Si-Cp)(OsBu)$_3$, Hf((CF$_3$)Me$_2$Si-Cp)(OnBu)$_3$, or Hf((CF$_3$)Me$_2$Si-Cp)(OiBu)$_3$.

Preferably, the Silicon- and Hafnium-containing precursor is (trimethylsilyl)cyclopentadienyl tris(dimethylamino) Hafnium(IV) or (trimethylsilyl)cyclopentadienyl tri(isopropoxy) Hafnium (IV).

the disclosed Hafnium-containing film forming compositions may be synthesized by reacting the corresponding tetrakis(amino) Hafnium(IV) or corresponding tetrakis (alkoxy) Hafnium(IV) with the corresponding (silyl) cyclopentadiene in a suitable solvent, such as toluene, THF or ether. (Silyl)cyclopentadiene are typically prepared according to the procedure described in Catal Lett (2011) 141:1625-1634. Alternatively the disclosed (silyl)cyclopentadienyl-tris(alkoxy) Hafnium-containing film forming composition may be synthesized by alcoholysis of the corresponding (silyl)cyclopentadienyl-tris(amino) Hafnium-containing compounds with 3 equivalents of the corresponding alcohol in a suitable solvent, such as toluene, THF or ether. However, an excess of alcohol in this synthesis process may result in unreacted reactants, such as Hf(NR$_2$)$_4$ or Hf(OR)$_4$, and unwanted reaction by-products, such as unsubstituted cyclopentadienyl reaction products like cyclopentadienyl tris(alkoxy) Hafnium or cyclopentadienyl tris (amino) Hafnium.

Purity of the disclosed Hafnium-containing film forming composition ranges from approximately 95% w/w to approximately 100% w/w, preferably higher than 98% w/w, and more preferably higher than 99% w/w. One of ordinary skill in the art will recognize that the purity may be determined by H NMR or gas or liquid chromatography with mass spectrometry. The disclosed Hafnium-containing film forming composition may contain any of the following impurities: HfCp(OR$^{10}$)$_3$; Hf(OR$^{10}$)$_4$; HfCp(NR$_2$)$_3$, with each R independently being H, a C1-C5 linear, branched or cyclic alkyl group, or a C1-C5 linear, branched, or cyclic fluoroalkyl group; Hf(NR$_2$)$_4$, with each R independently being H, a C1-C5 linear, branched or cyclic alkyl group, or a C1-C5 linear, branched, or cyclic fluoroalkyl group; cyclopentadiene; (silyl)cyclopentadiene; dicyclopentadiene; alkylsilanes; alkylamines such as tert-butylamine; dialkylamines such as dimethylamine; alkylimines; alcohol such as isopropylalcohol or tert-butylalcohol; THF; ether; pentane; cyclohexane; heptanes; toluene; benzene; chlorinated metal compounds; lithium, sodium, or potassium alkoxy; lithium, sodium, or potassium alkylamino; or lithium, potassium, or sodium cyclopentadienyl. The total quantity of these impurities is below 5% w/w, preferably below 2% w/w, and more preferably below 1% w/w. The composition may be purified by recrystallisation, sublimation, distillation, and/or passing the gas or liquid through a suitable adsorbent, such as a 4A molecular sieve.

Figure 2:
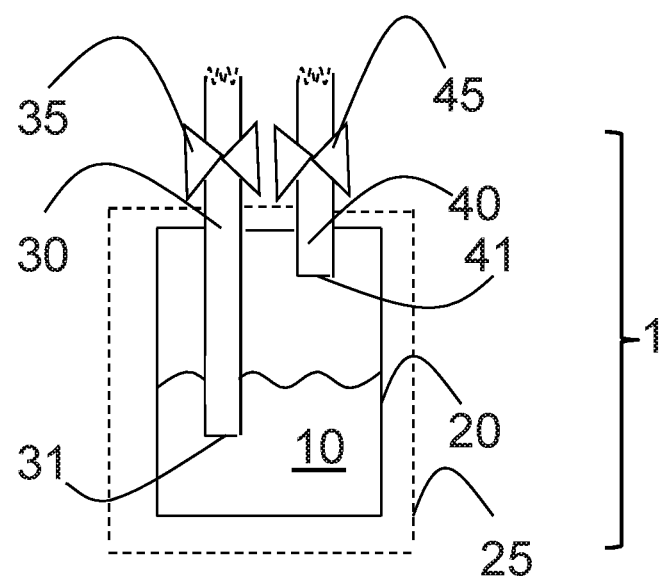
FIG. 2 is a side view of a second embodiment of the Hafnium-containing film forming delivery device disclosed herein.

Purification of the disclosed Hafnium-containing film forming compositions may also result in metal impurities at the 0 ppbw (part per billion weight) to 1 ppmw (parts per million weight) levels, preferably 0-500 ppbw. These metal impurities include, but are not limited to, Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), Vanadium (V) and Zinc (Zn).

the Hafnium-containing film forming compositions may be delivered to a semiconductor processing tool by the disclosed Hafnium-containing film forming composition delivery devices. FIGS. 1 and 2 show two non-limiting embodiments of the disclosed delivery devices 1.

FIG. 1 is a side view of one embodiment of the Hafnium-containing film forming composition delivery device 1. In FIG. 1, the disclosed Hafnium-containing film forming compositions 10 are contained within a container 20 having two conduits, an inlet conduit 30 and an outlet conduit 40. One of ordinary skill in the precursor art will recognize that the container 20, inlet conduit 30, and outlet conduit 40 are manufactured to prevent the escape of the gaseous form of the Hafnium-containing film forming composition 10, even at elevated temperature and pressure.

the delivery device 1 must be leak tight and be equipped with valves 35/45 that do not permit escape of even minute amounts of the material. Suitable valves 35/45 include spring-loaded or tied diaphragm valves. The valves 35/45 may further comprise a restrictive flow orifice (RFO). The delivery device 1 may be connected to a gas manifold (not shown) and in an enclosure (not shown). The gas manifold should permit the safe evacuation and purging of the piping that may be exposed to Air when the delivery device 1 is replaced so that any residual amounts of the Hf-containing film forming composition does not react. The enclosure may be equipped with sensors and fire control capability to control the fire in the case of material release or reaction. The gas manifold may also be equipped with isolation valves, vacuum generators, and permit the introduction of a purge gas at a minimum.

the delivery device 1 fluidly connects to other components of the semiconductor processing tool, such as the gas cabinet disclosed above, via valves 35 and 45. Preferably, the container 20, inlet conduit 30, valve 35, outlet conduit 40, and valve 45 are made of 316L EP or 304 stainless steel. However, one of ordinary skill in the art will recognize that other non-reactive materials may also be used in the teachings herein and that any corrosive Hafnium-containing film forming compositions 10 may require the use of more corrosion-resistant materials, such as Hastelloy or Inconel.

In FIG. 1, the end 31 of inlet conduit 30 is located above the surface of the Hafnium-containing film forming composition 10, whereas the end 41 of the outlet conduit 40 is located below the surface of the Hafnium-containing film forming composition 10. In this embodiment, the Hafnium-containing film forming composition 10 is preferably in liquid form. An inert gas, including but not limited to nitrogen, argon, helium, and mixtures thereof, may be introduced into the inlet conduit 30. The inert gas pressurizes the delivery device 20 so that the liquid Hafnium-containing film forming composition 10 is forced through the outlet conduit 40 and to components in the semiconductor processing tool (not shown). The semiconductor processing tool may include a vaporizer which transforms the liquid Hafnium-containing film forming composition 10 into a vapor, with or without the use of a carrier gas such as helium, argon, nitrogen or mixtures thereof, in order to deliver the vapor to a chamber where a wafer to be repaired is located and treatment occurs in the vapor phase. Alternatively, the liquid Hafnium-containing film forming composition 10 may be delivered directly to the wafer surface as a jet or aerosol.

FIG. 2 is a side view of a second embodiment of the Hafnium-containing film forming composition delivery device 1. In FIG. 2, the end 31 of inlet conduit 30 is located below the surface of the Hafnium-containing film forming composition 10, whereas the end 41 of the outlet conduit 40 is located above the surface of the Hafnium-containing film forming composition 10. FIG. 2 also includes an optional heating element 25, which may increase the temperature of the Hafnium-containing film forming composition 10. In this embodiment, the Hafnium-containing film forming composition 10 may be in solid or liquid form. An inert gas, including but not limited to nitrogen, argon, helium, and mixtures thereof, is introduced into the inlet conduit 30. The inert gas bubbles through the Hafnium-containing film forming composition 10 and carries a mixture of the inert gas and vaporized Hafnium-containing film forming composition 10 to the outlet conduit 40 and on to the components in the semiconductor processing tool.

Both FIGS. 1 and 2 include valves 35 and 45. One of ordinary skill in the art will recognize that valves 35 and 45 may be placed in an open or closed position to allow flow through conduits 30 and 40, respectively. Either delivery device 1 in FIG. 1 or 2, or a simpler delivery device having a single conduit terminating above the surface of any solid or liquid present, may be used if the Hafnium-containing film forming composition 10 is in vapor form or if sufficient vapor pressure is present above the solid/liquid phase. In this case, the Hafnium-containing film forming composition 10 is delivered in vapor form through the conduit 40 simply by opening the valve 45. The delivery device 1 may be maintained at a suitable temperature to provide sufficient vapor pressure for the Hafnium-containing film forming composition 10 to be delivered in vapor form, for example by the use of an optional heating element 25.

While FIGS. 1 and 2 disclose two embodiments of the Hafnium-containing film forming composition delivery device 1, one of ordinary skill in the art will recognize that the inlet conduit 30 and outlet conduit 40 may both be located above or below the surface 11 of the Hafnium-containing film forming composition 10 without departing from the disclosure herein. Furthermore, inlet conduit 30 may be a filling port. Finally, one of ordinary skill in the art will recognize that the disclosed Hafnium-containing film forming composition may be delivered to semiconductor processing tools using other delivery devices, such as the ampoules disclosed in WO 2006/059187 to Jurcik et al., without departing from the teachings herein.

Also disclosed are methods for forming Hafnium-containing layers on a substrate using a vapor deposition process. The method may be useful in the manufacture of semiconductor, photovoltaic, LCD-TFT, or flat panel type devices. The disclosed Hafnium-containing film forming compositions may be used to deposit thin Hafnium-containing films using any deposition methods known to those of skill in the art.

Examples of suitable deposition methods include, without limitation, chemical vapor deposition (CVD) or atomic layer deposition (ALD). Exemplary CVD methods include thermal CVD, plasma enhanced CVD (PECVD), pulsed CVD (PCVD), low pressure CVD (LPCVD), sub-atmospheric CVD (SACVD), atmospheric pressure CVD (APCVD), hot-wire CVD (HWCVD, also known as cat-CVD, in which a hot wire serves as an energy source for the deposition process), radicals incorporated CVD, and combinations thereof. Exemplary ALD methods include thermal ALD, plasma enhanced ALD (PEALD), spatial isolation ALD, hot-wire ALD (HWALD), radicals incorporated ALD, and combinations thereof. Supercritical fluid deposition may also be used. The deposition method is preferably ALD, PE-ALD, or spatial ALD in order to provide suitable step coverage and film thickness control.

the cubic/tetragonal crystalline phase of $HfO_2$ provides the highest dielectric constant of the different $HfO_2$ crystalline forms (cubic, tetragonal, amorphous, monoclinic, orthorhombic, and combinations thereof are the available crystalline phases). It is experimentally reported that a doping level (3-12%) of small ionic radius tetravalent dopant such as Si is the most efficient in stabilizing the tetragonal hafnium oxide phase. The substitution of a Hf atom by Si in the tetragonal $HfO_2$ structure results in reduced Si—O bond with length similar to that in $SiO_2$. Therefore, $HfO_2$ is an excellent host for Si, which is easily incorporated into the "friendly" local environment of the oxide (Cf., J. Appl. Phys. 106, 024107, 2009). The advantage is that Si is tetravalent therefore it substitutes Hf in the lattice without introducing O vacancies.

Alternatively, the amorphous phase of the hafnium-containing film may be desired. Amorphous hafnium oxide films are frequently used in optical filters, ultraviolet heat mirrors, or antireflective coatings. The amorphous hafnium-containing film may comprise between approximately 1 at. % and approximately 15 at. % Si. The use of amorphous hafnium oxide film for optical applications may require a thickness ranging from approximately 10 nm to approximately 100 nm.

Applicants believe that vapor deposition using the disclosed precursors and a suitable oxygen-containing reactant may provide a hafnium oxide film having suitable Si doping levels to obtain either the cubic/tetragonal or amorphous phase films. More particularly, a cyclic vapor deposition process using the disclosed precursors and $O_3$ may produce thick (i.e., 10 to 100 nm) amorphous $HfO_2$ films having a Si doping concentration of approximately 1at. % and approximately 30 at. % Si. In contrast, an ALD process using the disclosed precursors and $H_2O$ may produce cubic/tetragonal $HfO_2$ films having a Si doping concentration of approximately 1 at. % to approximately 5 at. % at temperatures ranging from approximately 250° C. to approximately 400° C.

Applicants believe that the vapor deposition process conditions may be controlled so that Hf alone or both Hf and Si may be deposited in the Hafnium-containing layer. For instance adjusting the ALD parameters to exhibit some parasitic CVD might be useful to deposit a finite amount of Si in the $HfO_2$ layer. Alternatively the silicon content in $HfO_2$ film may be controlled by alternating the deposition of (Hf, Si)$O_2$ film using the disclosed Hafnium-containing film forming compositions and the deposition of $HfO_2$ using another Hafnium-containing precursor. For example, HfCp(NMe$_2$)$_3$, Hf(MeCp)(NMe$_2$)$_3$ or Hf(EtCp)(NMe$_2$)$_3$ may serve as the Hf-containing precursor to produce pure $HfO_2$ films. In other words x subcycles of (Hf, Si)$O_2$ deposition using the Hafnium-containing film forming compositions may be alternated with y subcycles of pure $HfO_2$ deposition using a Hafnium-containing precursor, such as HfCp(NMe$_2$)$_3$. The supercycle consisting of x subcycles of (Hf, Si)$O_2$ and y subcycles of pure $HfO_2$ may be repeated to obtain a desired thickness of (Hf, Si)$O_2$ film, wherein x and y are integers which inclusively range from 1 to 20. Hf and Si content may be controlled by adjusting x and y.

Alternatively the silicon content in the $HfO_2$ film may be controlled by depositing the (Hf, Si)$O_2$ film using a mixture containing both the disclosed Hafnium-containing film forming composition and a Hafnium-containing precursor. For example, HfCp(NMe$_2$)$_3$, Hf(MeCp)(NMe$_2$)$_3$, Hf(EtCp)(NMe$_2$)$_3$, Hf(iPrCp)(NMe$_2$)$_3$, or Hf(tBuCp)(NMe$_2$)$_3$ may serve as the Hf-containing precursor. The Hf and Si content may be controlled by adjusting the ratio between the Hafnium-containing film forming composition and the Hafnium-containing precursor in the mixture.

The disclosed Hafnium-containing film forming compositions may be supplied either in neat form or in a blend with a suitable solvent, such as ethyl benzene, xylene, mesitylene, decane, or dodecane. The disclosed compositions may be present in varying concentrations in the solvent.

The neat or blended Hafnium-containing film forming compositions are introduced into a reactor in vapor form by conventional means, such as tubing and/or flow meters. The composition in vapor form may be produced by vaporizing the neat or blended composition through a conventional vaporization step such as direct vaporization, distillation, direct liquid injection, or by bubbling, or by using a sublimator such as the one disclosed in PCT Publication WO2009/087609 to Xu et al. The neat or blended composition may be fed in liquid state to a vaporizer where it is vaporized before it is introduced into the reactor. Alternatively, the neat or blended composition may be vaporized by passing a carrier gas into a container containing the composition or by bubbling the carrier gas into the composition. The carrier gas may include, but is not limited to, Ar, He, $N_2$, and mixtures thereof. Bubbling with a carrier gas may also remove any dissolved oxygen present in the neat or blended composition. The carrier gas and composition are then introduced into the reactor as a vapor.

If necessary, the container of disclosed composition may be heated to a temperature that permits the composition to be in its liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of composition vaporized.

The reactor may be any enclosure or chamber within a device in which deposition methods take place such as without limitation, a parallel-plate type reactor, a cold-wall type reactor, a hot-wall type reactor, a single-wafer reactor, a multi-wafer reactor (i.e., a batch reactor), or other types of deposition systems under conditions suitable to cause the precursor to react and form the layers.

Generally, the reactor contains the substrate(s) onto which the thin films will be deposited. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, silica, glass, or GaAs wafers. The wafer may have one or more layers of differing materials deposited on it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, or combination thereof. Additionally, the wafers may include copper layers, tungsten layers, or noble metal layers (e.g., platinum, palladium rhodium, or gold). Plastic layers, such as poly(3,4-ethylenedioxythiophene)

poly (styrenesulfonate) [PEDOT:PSS], may also be used. The layers may be planar or patterned.

The disclosed processes may deposit the Hf-containing layer directly on the wafer or directly on one or more than one (when patterned layers from the substrate) of the layers on top of the wafer. The substrate may be patterned to include vias or trenches having high aspect ratios. For example, a conformal Hf-containing film, such as $HfO_2$, may be deposited using any ALD technique on a through silicon via (TSV) having an aspect ratio ranging from approximately 20:1 to approximately 100:1. Furthermore, one of ordinary skill in the art will recognize that the terms "film" or "layer" used herein refer to a thickness of some material laid on or spread over a surface and that the surface may be a trench or a line. Throughout the specification and claims, the wafer and any associated layers thereon are referred to as substrates. For example, a $HfO_2$ film may be deposited onto a TiN substrate. In subsequent processing, a TiN layer may be deposited on the $HfO_2$ layer, forming a TiN/$HfO_2$/TiN stack used as DRAM capacitor.

The temperature and the pressure within the reactor are held at conditions suitable for vapor depositions. In other words, after introduction of the vaporized composition into the chamber, conditions within the chamber are such that at least part of the precursor is deposited onto the substrate to form a Hafnium-containing film. For instance, the pressure in the reactor may be held between about 1 Pa and about $10^5$ Pa, more preferably between about 25 Pa and about $10^3$ Pa, as required per the deposition parameters. Likewise, the temperature in the reactor may be held between about 100° C. and about 500° C., preferably between about 150° C. and about 400° C. One of ordinary skill in the art will recognize that "at least part of the precursor is deposited" means that some or all of the precursor in the disclosed Hf-containing film forming compositions reacts with or adheres to the substrate, either by itself or with the aid of a reactant.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 100° C. to approximately 500° C. When a plasma deposition process is utilized, the deposition temperature may range from approximately 150° C. to approximately 400° C. Alternatively, when a thermal process is performed, the deposition temperature may range from approximately 200° C. to approximately 500° C.

In addition to the disclosed precursor, a reactant may also be introduced into the reactor. The reactant may be an oxidizing gas such as $O_2$, $O_3$, $H_2O$, $H_2O_2$, NO, $N_2O$, $NO_2$, oxygen containing radicals such as O* or OH*, NO, $NO_2$, carboxylic acids, formic acid, acetic acid, propionic acid, and mixtures thereof. $O_2$ may include $^1\Delta_g$ singlet oxygen, $^1\Sigma_g^+$ singlet oxygen, the conventional $^3\Sigma_g^-$ triplet oxygen, or combinations thereof. The higher energy states of $O_2$ may be generated using electric discharge, irradiation of a photosensitizer such as that disclosed by Ito et al. in JP2012/087025, or by a MEMS chip, such as the one disclosed by Velásquez-García et al. (J Microelectromechanical Systems Vol. 16, No. 6, December 2007). Applicants believe that a mixture of singlet oxygen with triplet oxygen and/or ozone may provide suitable reactivity without damaging the underlying substrate due to the short lifespan of the higher energy state $O_2$. Alternatively, the oxidizing gas is selected from the group consisting of $O_2$, $O_3$, $H_2O$, $H_2O_2$, oxygen containing radicals thereof such as $O^{\cdot 1}$ or $OH^{\cdot 1}$, and mixtures thereof.

Alternatively, the reactant may be a reducing gas such as $H_2$, $H_2CO$, $NH_3$, $SiH_4$, $Si_2H_6$, $Si_3H_8$, $(CH_3)_2SiH_2$, $(C_2H_5)_2SiH_2$, $(CH_3)SiH_3$, $(C_2H_5)SiH_3$, phenyl silane, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenyl hydrazine, N-containing molecules, $B_2H_6$, 9-borabicyclo[3,3,1] nonane, dihydrobenzenfuran, pyrazoline, trimethylaluminium, dimethylzinc, diethylzinc, radical species thereof, and mixtures thereof. Preferably, the reducing gas is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof.

The reactant may be treated by plasma, in order to decompose the reactant into its radical form. $N_2$ may also be utilized as a reducing gas when treated with plasma. For instance, the plasma may be generated with a power ranging from about 50 W to about 500 W, preferably from about 100 W to about 400 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

For example, the reactant may be introduced into a direct plasma reactor, which generates plasma in the reaction chamber, to produce the plasma-treated reactant in the reaction chamber. Exemplary direct plasma reactors include the Titan™ PECVD System produced by Trion Technologies. The reactant may be introduced and held in the reaction chamber prior to plasma processing. Alternatively, the plasma processing may occur simultaneously with the introduction of the reactant. In-situ plasma is typically a 13.56 MHz RF inductively coupled plasma that is generated between the showerhead and the substrate holder. The substrate or the showerhead may be the powered electrode depending on whether positive ion impact occurs. Typical applied powers in in-situ plasma generators are from approximately 30 W to approximately 1000 W. Preferably, powers from approximately 30 W to approximately 600 W are used in the disclosed methods. More preferably, the powers range from approximately 100 W to approximately 500 W. The disassociation of the reactant using in-situ plasma is typically less than achieved using a remote plasma source for the same power input and is therefore not as efficient in reactant disassociation as a remote plasma system, which may be beneficial for the deposition of Hafnium-containing films on substrates easily damaged by plasma.

Alternatively, the plasma-treated reactant may be produced outside of the reaction chamber. The MKS Instruments' ASTRONi® reactive gas generator may be used to treat the reactant prior to passage into the reaction chamber. Operated at 2.45 GHz, 7 kW plasma power, and a pressure ranging from approximately 0.5 Torr to approximately 10 Torr, the reactant $O_2$ may be decomposed into two O' radicals. Preferably, the remote plasma may be generated with a power ranging from about 1 kW to about 10 kW, more preferably from about 2.5 kW to about 7.5 kW.

the vapor deposition conditions within the chamber allow the disclosed precursors and the reactant to react and form a Hafnium-containing film on the substrate. In some embodiments, Applicants believe that plasma-treating the reactant may provide the reactant with the energy needed to react with the disclosed precursor.

Depending on what type of film is desired to be deposited, an additional precursor compound may be introduced into the reactor. The additional precursor may be used to provide the same (i.e., Hf) or additional elements to the Hafnium-containing film. The additional elements may include hafnium, niobium, tanatalum, lanthanides (Ytterbium, Erbium, Dysprosium, Gadolinium, Praseodymium, Cerium, Lanthanum, Yttrium), germanium, silicon, titanium, manganese, cobalt, nickel, ruthenium, bismuth, lead, magnesium, aluminum, or mixtures of these. When an additional precursor is utilized, the resultant film deposited on the substrate may contain the Hafnium in combination with at least one additional element.

the Hafnium-containing film forming compositions and reactants may be introduced into the reactor either simultaneously (chemical vapor deposition), sequentially (atomic layer deposition), or different combinations thereof. The reactor may be purged with an inert gas between the introduction of the composition and the introduction of the reactant. Alternatively, the reactant and the composition may be mixed together to form a reactant/composition mixture, and then introduced to the reactor in mixture form. Another example is to introduce the reactant continuously and to introduce the Hafnium-containing film forming composition by pulse (pulsed chemical vapor deposition).

The vaporized composition and the reactant may be pulsed sequentially or simultaneously (e.g. pulsed CVD) into the reactor. Each pulse of composition may last for a time period ranging from about 0.01 seconds to about 10 seconds, alternatively from about 0.3 seconds to about 3 seconds, alternatively from about 0.5 seconds to about 2 seconds. In another embodiment, the reactant may also be pulsed into the reactor. In such embodiments, the pulse of each gas may last for a time period ranging from about 0.01 seconds to about 10 seconds, alternatively from about 0.3 seconds to about 3 seconds, alternatively from about 0.5 seconds to about 2 seconds. In another alternative, the vaporized composition and one or more reactants may be simultaneously sprayed from a shower head under which a susceptor holding several wafers is spun (spatial ALD).

Depending on the particular process parameters, deposition may take place for a varying length of time. Generally, deposition may be allowed to continue as long as desired or necessary to produce a film with the necessary properties. Typical thin film thicknesses may vary from several angstroms to several hundreds of microns, depending on the specific deposition process. The deposition process may also be performed as many times as necessary to obtain the desired film thickness.

In one non-limiting exemplary CVD type process, the vapor phase of the disclosed Hafnium-containing film forming composition and a reactant are simultaneously introduced into the reactor. The two react to form the resulting Hafnium-containing thin film. When the reactant in this exemplary CVD process is treated with plasma, the exemplary CVD process becomes an exemplary PECVD process. The reactant may be treated with plasma prior or subsequent to introduction into the chamber.

In one non-limiting exemplary ALD type process, the vapor phase of the disclosed Hafnium-containing film forming composition is introduced into the reactor, where it is contacted with a suitable substrate. Excess composition may then be removed from the reactor by purging and/or evacuating the reactor. A reactant (for example, $H_2$) is introduced into the reactor where it reacts with the physi- or chem i-sorbed precursor in a self-limiting manner. Any excess reactant is removed from the reactor by purging and/or evacuating the reactor. If the desired film is a Hafnium film, this two-step process may provide the desired film thickness or may be repeated until a film having the necessary thickness has been obtained.

Alternatively, if the desired film contains Hafnium and a second element, the two-step process above may be followed by introduction of the vapor of an additional precursor compound into the reactor. The additional precursor compound will be selected based on the nature of the Hafnium film being deposited. After introduction into the reactor, the additional precursor compound is contacted with the substrate. Any excess precursor compound is removed from the reactor by purging and/or evacuating the reactor. Once again, a reactant may be introduced into the reactor to react with the physi- or chem i-sorbed precursor compound. Excess reactant gas is removed from the reactor by purging and/or evacuating the reactor. If a desired film thickness has been achieved, the process may be terminated. However, if a thicker film is desired, the entire four-step process may be repeated. By alternating the provision of the Hafnium-containing film forming composition, additional precursor compound, and reactant, a film of desired composition and thickness can be deposited.

When the reactant in this exemplary ALD process is treated with plasma, the exemplary ALD process becomes an exemplary PEALD process. The reactant may be treated with plasma prior or subsequent to introduction into the chamber.

In a second non-limiting exemplary ALD type process, the vapor phase of one of the disclosed Hf-containing film forming compositions, for example (trimethylsilyl)cyclopentadienyl tris(dimethylamino) Hafnium(IV), is introduced into the reactor, where it is contacted with a TiN substrate. Excess Hf-containing film forming composition may then be removed from the reactor by purging and/or evacuating the reactor. A reactant (for example, $O_3$) is introduced into the reactor where it reacts with the physi- or chemi-sorbed precursor in a self-limiting manner to form a $HfO_2$ or (Hf, Si)$O_2$ film. Any excess reactant is removed from the reactor by purging and/or evacuating the reactor. These two steps may be repeated until the $HfO_2$ or (Hf, Si)$O_2$ film obtains a desired thickness. A TiN layer may then be deposited on top of the $HfO_2$ or (Hf, Si)$O_2$ layer. The resulting TiN/$HfO_2$/TiN or TiN/(Hf, Si)$O_2$/TiN stack may be used in DRAM capacitors.

In a third non-limiting exemplary ALD type process, the vapor phase of one of the disclosed Hf-containing film forming compositions, for example (trimethylsilyl)cyclopentadienyl tris(dimethylamino) Hafnium(IV), is introduced in a first step into the reactor, where it is contacted with a TiN substrate. Excess Hf-containing film forming composition may then be removed from the reactor by purging and/or evacuating the reactor. A reactant (for example, $O_3$) is introduced into the reactor where it reacts with the chemi- or physi-sorbed precursor in a self-limiting manner to form a (Hf, Si)$O_2$ film. Any excess reactant is removed from the reactor by purging and/or evacuating the reactor. These two steps may be considered as a subcycle and may be repeated x times to obtain a desired thickness of (Hf, Si)$O_2$ film.

In a second step the vapor phase of a Hf-containing precursor, for example (methyl)cyclopentadienyl tris(dimethylam mo) Hafnium(IV) or (ethyl)cyclopentadienyl tris(dimethylamino) Hafnium(IV), is introduced into the same reactor. Excess Hf-containing precursor may then be removed from the reactor by purging and/or evacuating the reactor. A reactant (for example, $O_3$) is introduced into the reactor where it reacts with the chemi- or physi-sorbed Hf-containing precursor in a self-limiting manner to form a HfO$_2$ film. Any excess reactant is removed from the reactor by purging and/or evacuating the reactor. These two steps may be considered as a subcycle and may be repeated y time to obtain a desired thickness of pure HfO$_2$ film. The supercycle consisting of x subcycles of (Hf, Si)O$_2$ and y subcycles of HfO$_2$ may be be repeated to obtain a desired thickness of (Hf, Si)O$_2$ film. Hf and Si content may be controlled by adjusting the number of x and y cycles (x and y may independently range from 1 to 20). A TiN layer may then be deposited on top of the HfO$_2$ or (Hf, Si)O$_2$ layer. The resulting TiN/HfO$_2$/TiN or TiN/(Hf, Si)O$_2$/TiN stack may be used in DRAM capacitors.

In a fourth non-limiting exemplary ALD type process, the vapor phase of a mixture containing the disclosed Hf-containing film forming composition, for example (trimethylsilyl)cyclopentadienyl tris(dimethylamino) Hafnium(IV), and a Hf-containing precursor, for example (isopropyl) cyclopentadienyl tris(dimethylamino) Hafnium(IV) or (tert-butyl)cyclopentadienyl tris(dimethylamino) Hafnium(IV), is introduced into the reactor, where it is contacted with a substrate, for example TiN, NbN, Ru, TiO$_2$, MoO$_2$ or MoO$_3$. Excess mixture may then be removed from the reactor by purging and/or evacuating the reactor. A reactant (for example, O$_3$) is introduced into the reactor where it reacts with the chemi- or physi-sorbed precursors in a self-limiting manner to form a (Hf, Si)O$_2$ film. Any excess reactant is removed from the reactor by purging and/or evacuating the reactor. These two steps may be repeated until the (Hf, Si)O$_2$ film obtains a desired thickness. The Hf and Si content may be controlled by adjusting the ratio between the Hafnium-containing film forming composition and the Hafnium-containing precursor in the mixture. A TiN layer may be deposited on top of the (Hf, Si)O$_2$ layer. The resulting TiN/HfO$_2$/TiN or TiN/(Hf, Si)O$_2$/TiN stack may be used in DRAM capacitors.

the Hafnium-containing films resulting from the processes discussed above may include a pure Hafnium, Hafnium silicide (Hf$_k$Si$_l$), Hafnium oxide (Hf$_m$O$_n$), Silicon-doped Hafnium oxide (Hf$_o$Si$_p$O$_q$), Hafnium nitride (Hf$_r$N$_s$), or silicon-doped Hafnium nitride (Hf$_t$Si$_u$N$_v$), wherein k, l, m, n, o, p, q, r, s, t, u, and v are integers which inclusively range from 1 to 6. One of ordinary skill in the art will recognize that by judicial selection of the appropriate disclosed Hf-containing film forming compositions, optional precursor compounds, and reactant species, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the Hafnium-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 400° C. for 3600 seconds under a H-containing atmosphere or an O-containing atmosphere. The resulting film may contain fewer impurities and therefore may have an improved density resulting in improved leakage current. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the Hafnium-containing film. This in turn tends to improve the resistivity of the film.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:

1. A Hafnium-containing film forming composition comprising a silicon- and germanium-containing precursor having one of the following formulae:

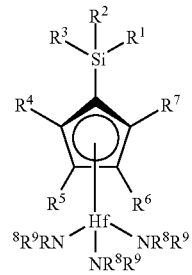

Formula I

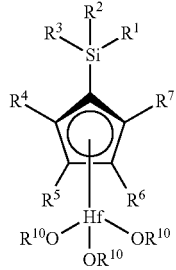

Formula II wherein each $R^1$, $R^2$, $R^3$, $R^4$, $R^5$, $R^6$, $R^7$, $R^8$, $R^9$ and $R^{10}$ is independently selected from H; a C1-C5 linear, branched, or cyclic alkyl group; or a C1-C5 linear, branched, or cyclic fluoroalkyl group.

2. The Hafnium-containing film forming composition of claim 1, the precursor having the Formula I:

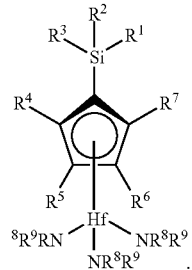

Formula I

3. The Hafnium-containing film forming composition of claim 2, wherein the precursor is selected from the group consisting of:

(trimethylsilyl)cyclopentadienyl tris(Dimethylamino) Hafnium(IV) (Hf(TMS-Cp)(NMe$_2$)$_3$); (trimethylsilyl)cyclopentadienyl tris(methylamino) Hafnium(IV) (Hf(TMS-Cp)(NHMe)$_3$); (trimethylsilyl)cyclopentadienyl tris(Diethylamino) Hafnium(IV) (Hf(TMS-Cp)(Net$_2$)$_3$); (trimethylsilyl)cyclopentadienyl tris(ethylamino) Hafnium(IV) (Hf(TMS-Cp)(NHEt)$_3$); (trimethylsilyl)cyclopentadienyl tris(ethylmethylamino) Hafnium(IV) (Hf(TMS-Cp)(NEtMe)$_3$); (trimethylsilyl)cyclopentadienyl tris(Di n-propylamino) Hafnium(IV) (Hf(TMS-Cp)(NnPr$_2$)$_3$); (trimethylsilyl)cyclopentadienyl tris(n-propylamino) Hafnium(IV) (Hf(TMS-Cp)(NHnPr)$_3$);

(trimethylsilyl)cyclopentadienyl tris(Di isopropylamino) Hafnium(IV) (Hf(TMS-Cp)(NiPr$_2$)$_3$); (trimethylsilyl)cyclopentadienyl tris(isopropylamino) Hafnium(IV) (Hf(TMS-Cp)(NHiPr)$_3$); (trimethylsilyl)cyclopentadienyl tris(Di n-butylamino) Hafnium(IV) (Hf(TMS-Cp)(NnBu$_2$)$_3$); (trimethylsilyl)cyclopentadienyl tris(n-butylamino) Hafnium(IV) (Hf(TMS-Cp)(NHnBu)$_3$) (trimethylsilyl)cyclopentadienyl tris(Di isobutylamino) Hafnium(IV) (Hf(TMS-Cp)(NiBu$_2$)$_3$);

(trimethylsilyl)cyclopentadienyl tris(isobutylamino) Hafnium(IV) (Hf(TMS-Cp)(NHiBu)$_3$); (trimethylsilyl)cyclopentadienyl tris(Di sec-butylamino) Hafnium(IV) (Hf(TMS-Cp)(NsBu$_2$)$_3$); (trimethylsilyl)cyclopentadienyl tris(sec-butylamino) Hafnium(IV) (Hf(TMS-Cp)(NHsBu)$_3$); (trimethylsilyl)cyclopentadienyl tris(Di tert-butylamino) Hafnium(IV) (Hf(TMS-Cp)(NtBu$_2$)$_3$); (trimethylsilyl)cyclopentadienyl tris(tert-butylamino) Hafnium(IV) (Hf(TMS-Cp)(NHtBu)$_3$);

(dimethylsilyl)cyclopentadienyl tris(Dimethylamino) Hafnium(IV) (Hf(DMS-Cp)(NMe$_2$)$_3$); (dimethylsilyl)cyclopentadienyl tris(methylamino) Hafnium(IV) (Hf(DMS-Cp)(NHMe)$_3$); (dimethylsilyl)cyclopentadienyl tris(Diethylamino) Hafnium(IV) (Hf(DMS-Cp)(Net$_2$)$_3$); (dimethylsilyl)cyclopentadienyl tris(ethylamino) Hafnium(IV) (Hf(DMS-Cp)(NHEt)$_3$); (dimethylsilyl)cyclopentadienyl tris(ethylmethylamino) Hafnium(IV) (Hf(DMS-Cp)(NEtMe)$_3$); (dimethylsilyl)cyclopentadienyl tris(Di n-propylamino) Hafnium(IV) (Hf(DMS-Cp)(NnPr$_2$)$_3$); (dimethylsilyl)cyclopentadienyl tris(n-propylamino) Hafnium(IV) (Hf(DMS-Cp)(NHnPr)$_3$);

(dimethylsilyl)cyclopentadienyl tris(Di isopropylamino) Hafnium(IV) (Hf(DMS-Cp)(NiPr$_2$)$_3$); (dimethylsilyl)cyclopentadienyl tris(isopropylamino) Hafnium(IV) (Hf(DMS-Cp)(NHiPr)$_3$); (dimethylsilyl)cyclopentadienyl tris(Di n-butylamino) Hafnium(IV) (Hf(DMS-Cp)(NnBu$_2$)$_3$); (dimethylsilyl)cyclopentadienyl tris(n-butylamino) Hafnium(IV) (Hf(DMS-Cp)(NHnBu)$_3$); (dimethylsilyl)cyclopentadienyl tris(Di isobutylamino) Hafnium(IV) (Hf(DMS-Cp)(NiBu$_2$)$_3$);

(dimethylsilyl)cyclopentadienyl tris(isobutylamino) Hafnium(IV) (Hf(DMS-Cp)(NHiBu)$_3$); (dimethylsilyl)cyclopentadienyl tris(Di sec-butylamino) Hafnium(IV) (Hf(DMS-Cp)(NsBu$_2$)$_3$); (dimethylsilyl)cyclopentadienyl tris(sec-butylamino) Hafnium(IV) (Hf(DMS-Cp)(NHsBu)$_3$); (dimethylsilyl)cyclopentadienyl tris(Di tert-butylamino) Hafnium(IV) (Hf(DMS-Cp)(NtBu$_2$)$_3$); (dimethylsilyl)cyclopentadienyl tris(tert-butylamino) Hafnium(IV) (Hf(DMS-Cp)(NHtBu)$_3$);

(trifluorosilyl)cyclopentadienyl tris(Dimethylamino) Hafnium(IV) (Hf(F$_3$Si-Cp)(NMe$_2$)$_3$); (trifluorosilyl)cyclopentadienyl tris(methylamino) Hafnium(IV) (Hf(F$_3$Si-Cp)(NHMe)$_3$); (trifluorosilyl)cyclopentadienyl tris(Diethylamino) Hafnium(IV) (Hf(F$_3$Si-Cp)(Net$_2$)$_3$); (trifluorosilyl)cyclopentadienyl tris(ethylamino) Hafnium(IV) (Hf(F$_3$Si-Cp)(NHEt)$_3$); (trifluorosilyl)cyclopentadienyl tris(Ethylmethylamino) Hafnium(IV) (Hf(F$_3$Si-Cp)(NEtMe)$_3$); (trifluorosilyl)cyclopentadienyl tris(Di n-propylamino) Hafnium(IV) (Hf(F$_3$Si-Cp)(NnPr$_2$)$_3$); (trifluorosilyl)cyclopentadienyl tris(n-propylamino) Hafnium(IV) (Hf(F$_3$Si-Cp)(NHnPr)$_3$) (trifluorosilyl)cyclopentadienyl tris(Di isopropylamino) Hafnium(IV) (Hf(F$_3$Si-Cp)(NiPr$_2$)$_3$); (trifluorosilyl)cyclopentadienyl tris(isopropylamino) Hafnium(IV) (Hf(F$_3$Si-Cp)(NHiPr)$_3$); (trifluorosilyl)cyclopentadienyl tris(Di n-butylamino) Hafnium(IV) (Hf(F$_3$Si-Cp)(NnBu$_2$)$_3$); (trifluorosilyl)cyclopentadienyl tris(n-butylamino) Hafnium(IV) (Hf(F$_3$Si-Cp)(NHnBu)$_3$); (trifluorosilyl)cyclopentadienyl tris(Di isobutylamino) Hafnium(IV) (Hf(F$_3$Si-Cp)(NiBu$_2$)$_3$); (trifluorosilyl)cyclopentadienyl tris(isobutylamino) Hafnium(IV) (Hf(F$_3$Si-Cp)(NHiBu)$_3$);

(trifluorosilyl)cyclopentadienyl tris(Di sec-butylamino) Hafnium(IV) (Hf(F$_3$Si-Cp)(NsBu$_2$)$_3$); (trifluorosilyl)cyclopentadienyl tris(sec-butylamino) Hafnium(IV) (Hf(F$_3$Si-Cp)(NHsBu)$_3$); (trifluorosilyl)cyclopentadienyl tris(Di tert-butylamino) Hafnium(IV) (Hf(F$_3$Si-Cp)(NtBu$_2$)$_3$); (trifluorosilyl)cyclopentadienyl tris(tert-butylamino) Hafnium(IV) (Hf(F$_3$Si-Cp)(NHtBu)$_3$); (difluorosilyl)cyclopentadienyl tris(Dimethylamino) Hafnium(IV) (Hf(F$_2$HSi-Cp)(NMe$_2$)$_3$); (difluorosilyl)cyclopentadienyl tris(methylamino) Hafnium(IV) (Hf(F$_2$HSi-Cp)(NHMe)$_3$); (difluorosilyl)cyclopentadienyl tris(Diethylamino) Hafnium(IV) (Hf(F$_2$HSi-Cp)(Net$_2$)$_3$); (difluorosilyl)cyclopentadienyl tris(ethylamino) Hafnium(IV) (Hf(F$_2$HSi-Cp)(NHEt)$_3$); (difluorosilyl)cyclopentadienyl tris(Ethylmethylamino) Hafnium(IV) (Hf(F$_2$HSi-Cp)(NEtMe)$_3$); (difluorosilyl)cyclopentadienyl tris(Di n-propylamino) Hafnium(IV) (Hf(F$_2$HSi-Cp)(NnPr$_2$)$_3$); (difluorosilyl)cyclopentadienyl tris(n-propylamino) Hafnium(IV) (Hf(F$_2$HSi-Cp)(NHnPr)$_3$); (difluorosilyl)cyclopentadienyl tris(Di isopropylamino) Hafnium(IV) (Hf(F$_2$HSi-Cp)(NiPr$_2$)$_3$); (difluorosilyl)cyclopentadienyl tris(isopropylamino) Hafnium(IV) (Hf(F$_2$HSi-Cp)(NHiPr)$_3$);

(difluorosilyl)cyclopentadienyl tris(Di n-butylamino) Hafnium(IV) (Hf(F$_2$HSi-Cp)(NnBu$_2$)$_3$); (difluorosilyl)cyclopentadienyl tris(n-butylamino) Hafnium(IV) (Hf(F$_2$HSi-Cp)(NHnBu)$_3$); (difluorosilyl)cyclopentadienyl tris(Di isobutylamino) Hafnium(IV) (Hf(F$_2$HSi-Cp)(NiBu$_2$)$_3$); (difluorosilyl)cyclopentadienyl tris(isobutylamino) Hafnium(IV) (Hf(F$_2$HSi-Cp)(NHiBu)$_3$);

(difluorosilyl)cyclopentadienyl tris(Di sec-butylamino) Hafnium(IV) (Hf(F$_2$HSi-Cp)(NsBu$_2$)$_3$); (difluorosilyl)cyclopentadienyl tris(sec-butylamino) Hafnium(IV) (Hf(F$_2$HSi-Cp)(NHsBu)$_3$); (difluorosilyl)cyclopentadienyl tris(Di tert-butylamino) Hafnium(IV) (Hf(F$_2$HSi-Cp)(NtBu$_2$)$_3$); (difluorosilyl)cyclopentadienyl tris(tert-butylamino) Hafnium(IV) (Hf(F$_2$HSi-Cp)(NHtBu)$_3$); (monofluorosilyl)cyclopentadienyl tris(Dimethylamino) Hafnium(IV) (Hf(FH$_2$Si-Cp)(NMe$_2$)$_3$); (monofluorosilyl)cyclopentadienyl tris(methylamino) Hafnium(IV) (Hf(FH$_2$Si-Cp)(NHMe)$_3$); (monofluorosilyl)cyclopentadienyl tris(Diethylamino) Hafnium(IV) (Hf(FH$_2$Si-Cp)(Net$_2$)$_3$); (monofluorosilyl)cyclopentadienyl tris(ethylamino) Hafnium(IV) (Hf(FH$_2$Si-Cp)(NHEt)$_3$); (monofluorosilyl)cyclopentadienyl tris(Ethylmethylamino) Hafnium(IV) (Hf(FH$_2$Si-Cp)(NEtMe)$_3$);

(monofluorosilyl)cyclopentadienyl tris(Di n-propylamino) Hafnium(IV) (Hf(FH$_2$Si-Cp)(NnPr$_2$)$_3$); (monofluorosilyl)cyclopentadienyl tris(n-propylamino) Hafnium(IV) (Hf(FH$_2$Si-Cp)(NHnPr)$_3$); (monofluorosilyl)cyclopentadienyl tris(Di isopropylamino) Hafnium(IV) (Hf(FH$_2$Si-Cp)(NiPr$_2$)$_3$); (monofluorosilyl) cyclopentadienyl tris(isopropylamino) Hafnium(IV) (Hf(FH$_2$Si-Cp)(NHiPr)$_3$);

(monofluorosilyl)cyclopentadienyl tris(Di n-butylamino) Hafnium(IV) (Hf(FH$_2$Si-Cp)(NnBu$_2$)$_3$); (monofluorosilyl)cyclopentadienyl tris(n-butylamino) Hafnium (IV) (Hf(FH$_2$Si-Cp)(NHnBu)$_3$); (monofluorosilyl)cyclopentadienyl tris(Di isobutylamino) Hafnium(IV) (Hf(FH$_2$Si-Cp)(NiBu$_2$)$_3$) (monofluorosilyl)cyclopentadienyl tris(isobutylamino) Hafnium(IV) (Hf(FH$_2$Si-Cp)(NHiBu)$_3$);

(monofluorosilyl)cyclopentadienyl tris(Di sec-butylamino) Hafnium(IV) (Hf(FH$_2$Si-Cp)(NsBu$_2$)$_3$); (monofluorosilyl)cyclopentadienyl tris(sec-butylamino) Hafnium(IV) (Hf(FH$_2$Si-Cp)(NHsBu)$_3$); (monofluorosilyl)cyclopentadienyl tris(Di tert-butylamino) Hafnium(IV) (Hf(FH$_2$Si-Cp)(NtBu$_2$)$_3$); (monofluorosilyl)cyclopentadienyl tris(tert-butylamino) Hafnium(IV) (Hf(FH$_2$Si-Cp)(NHtBu)$_3$); (fluoro dimethylsilyl)cyclopentadienyl tris(Dimethylamino) Hafnium(IV) (Hf(FMe$_2$Si-Cp)(NMe$_2$)$_3$); (fluoro dimethylsilyl)cyclopentadienyl tris(methylamino) Hafnium(IV) (Hf(FMe$_2$Si-Cp)(NHMe)$_3$); (fluoro dimethylsilyl)cyclopentadienyl tris(Diethylamino) Hafnium(IV) (Hf(FMe$_2$Si-Cp)(Net$_2$)$_3$); (fluoro dimethylsilyl)cyclopentadienyl tris(ethylamino) Hafnium(IV) (Hf(FMe$_2$Si-Cp)(NHEt)$_3$); (fluoro dimethylsilyl)cyclopentadienyl tris(Ethylmethylamino) Hafnium (IV) (Hf(FMe$_2$Si-Cp)(NEtMe)$_3$); (fluoro dimethylsilyl) cyclopentadienyl tris(Di n-propylamino) Hafnium(IV) (Hf(FMe$_2$Si-Cp)(NnPr$_2$)$_3$); (fluoro dimethylsilyl)cyclopentadienyl tris(n-propylamino) Hafnium(IV) (Hf(FMe$_2$Si-Cp)(NHnPr)$_3$); (fluoro dimethylsilyl)cyclopentadienyl tris(Di isopropylamino) Hafnium(IV) (Hf(FMe$_2$Si-Cp)(NiPr$_2$)$_3$); (fluoro dimethylsilyl) cyclopentadienyl tris(isopropylamino) Hafnium(IV) (Hf(FMe$_2$Si-Cp)(NHiPr)$_3$); (fluoro dimethylsilyl)cyclopentadienyl tris(Di n-butylamino) Hafnium(IV) (Hf(FMe$_2$Si-Cp)(NnBu$_2$)$_3$); (fluoro dimethylsilyl)cyclopentadienyl tris(n-butylamino) Hafnium(IV) (Hf(FMe$_2$Si-Cp)(NHnBu)$_3$); (fluoro dimethylsilyl) cyclopentadienyl tris(Di isobutylamino) Hafnium(IV) (Hf(FMe$_2$Si-Cp)(NiBu$_2$)$_3$); (fluoro dimethylsilyl)cyclopentadienyl tris(isobutylamino) Hafnium(IV) (Hf(FMe$_2$Si-Cp)(NHiBu)$_3$); (fluoro dimethylsilyl)cyclopentadienyl tris(Di sec-butylamino) Hafnium(IV) (Hf(FMe$_2$Si-Cp)(NsBu$_2$)$_3$); (fluoro dimethylsilyl) cyclopentadienyl tris(sec-butylamino) Hafnium(IV) (Hf(FMe$_2$Si-Cp)(NHsBu)$_3$); (fluoro dimethylsilyl)cyclopentadienyl tris(Di tert-butylamino) Hafnium(IV) (Hf(FMe$_2$Si-Cp)(NtBu$_2$)$_3$); (fluoro dimethylsilyl)cyclopentadienyl tris(tert-butylamino) Hafnium(IV) (Hf(FMe$_2$Si-Cp)(NHtBu)$_3$);

(tris(trifluoromethyl)silyl)cyclopentadienyl tris(Dimethylamino) Hafnium(IV) (Hf((CF$_3$)$_3$Si-Cp)(NMe$_2$)$_3$); (tris(trifluoromethyl)silyl)cyclopentadienyl tris(methylamino) Hafnium(IV) (Hf((CF$_3$)$_3$Si-Cp)(NHMe)$_3$); (tris(trifluoromethyl)silyl)cyclopentadienyl tris(Diethylamino) Hafnium(IV) (Hf((CF$_3$)$_3$Si-Cp)(Net$_2$)$_3$); (tris(trifluoromethyl)silyl)cyclopentadienyl tris(ethylamino) Hafnium(IV) (Hf((CF$_3$)$_3$Si-Cp)(NHEt)$_3$); (tris(trifluoromethyl)silyl)cyclopentadienyl tris(Ethylmethylamino) Hafnium(IV) (Hf((CF$_3$)$_3$Si-Cp)(NEtMe)$_3$); (tris(trifluoromethyl)silyl)cyclopentadienyl tris(Di n-propylamino) Hafnium(IV) (Hf((CF$_3$)$_3$Si-Cp)(NnPr$_2$)$_3$); (tris(trifluoromethyl)silyl)cyclopentadienyl tris(n-propylamino) Hafnium(IV) (Hf((CF$_3$)$_3$Si-Cp)(NHnPr)$_3$); (tris(trifluoromethyl)silyl)cyclopentadienyl tris(Di isopropylamino) Hafnium(IV) (Hf((CF$_3$)$_3$Si-Cp)(NiPr$_2$)$_3$);

(tris(trifluoromethyl)silyl)cyclopentadienyl tris(isopropylamino) Hafnium(IV) (Hf((CF$_3$)$_3$Si-Cp)(NHiPr)$_3$); (tris(trifluoromethyl)silyl)cyclopentadienyl tris(Di n-butylamino) Hafnium(IV) (Hf((CF$_3$)$_3$Si-Cp)(NnBu$_2$)$_3$); (tris(trifluoromethyl)silyl)cyclopentadienyl tris(n-butylamino) Hafnium(IV) (Hf((CF$_3$)$_3$Si-Cp)(NHnBu)$_3$); (tris(trifluoromethyl)silyl)cyclopentadienyl tris(Di isobutylamino) Hafnium(IV) (Hf((CF$_3$)$_3$Si-Cp)(NiBu$_2$)$_3$); (tris(trifluoromethyl)silyl)cyclopentadienyl tris(isobutylamino) Hafnium(IV) (Hf((CF$_3$)$_3$Si-Cp)(NHiBu)$_3$);

(tris(trifluoromethyl)silyl)cyclopentadienyl tris(Di sec-butylamino) Hafnium(IV) (Hf((CF$_3$)$_3$Si-Cp)(NsBu$_2$)$_3$); (tris(trifluoromethyl)silyl)cyclopentadienyl tris(sec-butylamino) Hafnium(IV) (Hf((CF$_3$)$_3$Si-Cp)(NHsBu)$_3$); (tris(trifluoromethyl)silyl)cyclopentadienyl tris(Di tert-butylamino) Hafnium(IV) (Hf((CF$_3$)$_3$Si-Cp)(NtBu$_2$)$_3$); (tris(trifluoromethyl)silyl)cyclopentadienyl tris(tert-butylamino) Hafnium(IV) (Hf((CF$_3$)$_3$Si-Cp)(NHtBu)$_3$);

(bis(trifluoromethyl)silyl)cyclopentadienyl tris(Dimethylamino) Hafnium(IV) (Hf((CF$_3$)$_2$HSi-Cp)(NMe$_2$)$_3$); (bis(trifluoromethyl)silyl)cyclopentadienyl tris(methylamino) Hafnium(IV) (Hf((CF$_3$)$_2$HSi-Cp)(NHMe)$_3$); (bis(trifluoromethyl)silyl)cyclopentadienyl tris(Diethylamino) Hafnium(IV) (Hf((CF$_3$)$_2$HSi-Cp)(Net$_2$)$_3$); (bis(trifluoromethyl)silyl)cyclopentadienyl tris(ethylamino) Hafnium(IV) (Hf((CF$_3$)$_2$HSi-Cp)(NHEt)$_3$); (bis(trifluoromethyl)silyl)cyclopentadienyl tris(Ethylmethylamino) Hafnium(IV) (Hf((CF$_3$)$_2$HSi-Cp)(NEtMe)$_3$); (bis(trifluoromethyl)silyl)cyclopentadienyl tris(Di n-propylamino) Hafnium(IV) (Hf((CF$_3$)$_2$HSi-Cp)(NnPr$_2$)$_3$); (bis(trifluoromethyl)silyl)cyclopentadienyl tris(n-propylamino) Hafnium(IV) (Hf((CF$_3$)$_2$HSi-Cp)(NHnPr)$_3$); (bis(trifluoromethyl)silyl)cyclopentadienyl tris(Di isopropylamino) Hafnium(IV) (Hf((CF$_3$)$_2$HSi-Cp)(NiPr$_2$)$_3$); (bis(trifluoromethyl)silyl)cyclopentadienyl tris(isopropylamino) Hafnium(IV) (Hf((CF$_3$)$_2$HSi-Cp)(NHiPr)$_3$); (bis(trifluoromethyl)silyl)cyclopentadienyl tris(Di n-butylamino) Hafnium(IV) (Hf((CF$_3$)$_2$HSi-Cp)(NnBu$_2$)$_3$); (bis(trifluoromethyl)silyl)cyclopentadienyl tris(n-butylamino) Hafnium(IV) (Hf((CF$_3$)$_2$HSi-Cp)(NHnBu)$_3$); (bis(trifluoromethyl)silyl)cyclopentadienyl tris(Di isobutylamino) Hafnium(IV) (Hf((CF$_3$)$_2$HSi-Cp)(NiBu$_2$)$_3$); (bis(trifluoromethyl)silyl)cyclopentadienyl tris(isobutylamino) Hafnium(IV) (Hf((CF$_3$)$_2$HSi-Cp)(NHiBu)$_3$); (bis(trifluoromethyl)silyl)cyclopentadienyl tris(Di sec-butylamino) Hafnium(IV) (Hf((CF$_3$)$_2$HSi-Cp)(NsBu$_2$)$_3$); (bis(trifluoromethyl)silyl)cyclopentadienyl tris(sec-butylamino) Hafnium(IV) (Hf((CF$_3$)$_2$HSi-Cp)(NHsBu)$_3$); (bis(trifluoromethyl)silyl)cyclopentadienyl tris(Di tert-butylamino) Hafnium(IV) (Hf((CF$_3$)$_2$HSi-Cp)(NtBu$_2$)$_3$); (bis(trifluoromethyl)silyl)cyclopentadienyl tris(tert-butylamino) Hafnium(IV) (Hf((CF$_3$)$_2$HSi-Cp)(NHtBu)$_3$);

((trifluoromethyl)dimethylsilyl)cyclopentadienyl tris(Dimethylamino) Hafnium(IV) (Hf((CF$_3$)Me$_2$-Cp)(NMe$_2$)$_3$); ((trifluoromethyl)dimethylsilyl)cyclopentadienyl tris(methylamino) Hafnium(IV) (Hf((CF$_3$)Me$_2$-Cp)(NHMe)$_3$);

((trifluoromethyl)dimethylsilyl)cyclopentadienyl tris(Diethylamino) Hafnium(IV) (Hf((CF$_3$)Me$_2$-Cp)(Net$_2$)$_3$); ((trifluoromethyl)dimethylsilyl)cyclopentadienyl tris(ethylamino) Hafnium(IV) (Hf((CF$_3$)Me$_2$-Cp)(NHEt)$_3$);

((trifluoromethyl)dimethylsilyl)cyclopentadienyl tris(Ethylmethylamino) Hafnium(IV) (Hf((CF$_3$)Me$_2$-Cp)(NEtMe)$_3$); ((trifluoromethyl)dimethylsilyl)cyclopentadienyl tris(Di n-propylamino) Hafnium(IV) (Hf((CF$_3$)Me$_2$-Cp)(NnPr$_2$)$_3$);

((trifluoromethyl)dimethylsilyl)cyclopentadienyl tris(n-propylamino) Hafnium(IV) (Hf((CF$_3$)Me$_2$-Cp)(NHnPr)$_3$); ((trifluoromethyl)dimethylsilyl)cyclopentadienyl tris(Di isopropylamino) Hafnium(IV) (Hf((CF$_3$)Me$_2$-Cp)(NiPr$_2$)$_3$);

((trifluoromethyl)dimethylsilyl)cyclopentadienyl tris(isopropylamino) Hafnium(IV) (Hf((CF$_3$)Me$_2$-Cp)(NHiPr)$_3$); ((trifluoromethyl)dimethylsilyl)cyclopentadienyl tris(Di n-butylamino) Hafnium(IV) (Hf((CF$_3$)Me$_2$-Cp)(NnBu$_2$)$_3$);

((trifluoromethyl)dimethylsilyl)cyclopentadienyl tris(n-butylamino) Hafnium(IV) (Hf((CF$_3$)Me$_2$-Cp)(NHnBu)$_3$); ((trifluoromethyl)dimethylsilyl)cyclopentadienyl tris(Di isobutylamino) Hafnium(IV) (Hf((CF$_3$)Me$_2$-Cp)(NiBu$_2$)$_3$);

((trifluoromethyl)dimethylsilyl)cyclopentadienyl tris(isobutylamino) Hafnium(IV) (Hf((CF$_3$)Me$_2$-Cp)(NHiBu)$_3$); ((trifluoromethyl)dimethylsilyl)cyclopentadienyl tris(Di sec-butylamino) Hafnium(IV) (Hf((CF$_3$)Me$_2$-Cp)(NsBu$_2$)$_3$);

((trifluoromethyl)dimethylsilyl)cyclopentadienyl tris(sec-butylamino) Hafnium(IV) (Hf((CF$_3$)Me$_2$-Cp)(NHsBu)$_3$); ((trifluoromethyl)dimethylsilyl)cyclopentadienyl tris(Di tert-butylamino) Hafnium(IV) (Hf((CF$_3$)Me$_2$-Cp)(NtBu$_2$)$_3$); and ((trifluoromethyl)dimethylsilyl)cyclopentadienyl tris(tert-butylamino) Hafnium(IV) (Hf((CF$_3$)Me$_2$-Cp)(NHtBu)$_3$).

4. The Hafnium-containing film forming composition of claim 3, wherein the precursor is (trimethylsilyl)cyclopentadienyl tris(dimethylamino) Hafnium(IV) [Hf(TMS-Cp)(NMe$_2$)$_3$].

5. The Hafnium-containing film forming composition of claim 1, the precursor having the Formula II:

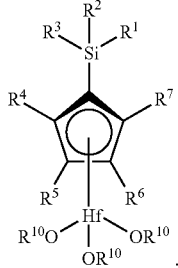

Formula II

6. The Hafnium-containing film forming composition of claim 5, wherein the precursor is selected from the group consisting of: (trimethylsilyl)cyclopentadienyl tris(methoxy) Hafnium(IV) (Hf(TMS-Cp)(OMe)$_3$); (trimethylsilyl)cyclopentadienyl tris(ethoxy) Hafnium(IV) (Hf(TMS-Cp)(OEt)$_3$); (trimethylsilyl)cyclopentadienyl tris(n-propoxy) Hafnium(IV) (Hf(TMS-Cp)(OnPr)$_3$); (trimethylsilyl)cyclopentadienyl tris(isopropoxy) Hafnium (IV) (Hf(TMS-Cp)(OiPr)$_3$); (trimethylsilyl)cyclopentadienyl tris(tert-butoxy) Hafnium(IV) (Hf(TMS-Cp)(OtBu)$_3$); (trimethylsilyl)cyclopentadienyl tris(sec-butoxy) Hafnium (IV) (Hf(TMS-Cp)(OsBu)$_3$); (trimethylsilyl)cyclopentadienyl tris(n-butoxy) Hafnium(IV) (Hf(TMS-Cp)(OnBu)$_3$); (trimethylsilyl)cyclopentadienyl tris(iso-butoxy) Hafnium (IV) (Hf(TMS-Cp)(OiBu)$_3$); (dimethylsilyl)cyclopentadienyl tris(methoxy) Hafnium(IV) (Hf(DMS-Cp)(OMe)$_3$); (dimethylsilyl)cyclopentadienyl tris(ethoxy) Hafnium(IV) (Hf(DMS-Cp)(OEt)$_3$); (dimethylsilyl)cyclopentadienyl tris(n-propoxy) Hafnium(IV) (Hf(DMS-Cp)(OnPr)$_3$); (dimethylsilyl)cyclopentadienyl tris(isopropoxy) Hafnium(IV) (Hf(DMS-Cp)(OiPr)$_3$); (dimethylsilyl)cyclopentadienyl tris(tert-butoxy) Hafnium(IV) (Hf(DMS-Cp)(OtBu)$_3$); (dimethylsilyl)cyclopentadienyl tris(sec-butoxy) Hafnium (IV) (Hf(DMS-Cp)(OsBu)$_3$); (dimethylsilyl)cyclopentadienyl tris(n-butoxy) Hafnium(IV) (Hf(DMS-Cp)(OnBu)$_3$); (dimethylsilyl)cyclopentadienyl tris(isobutoxy) Hafnium (IV) (Hf(DMS-Cp)(OiBu)$_3$); (trifluorosilyl)cyclopentadienyl tris(methoxy) Hafnium(IV) (Hf(F$_3$SiCp)(OMe)$_3$);

(trifluorosilyl)cyclopentadienyl tris(ethoxy) Hafnium(IV) (Hf(F$_3$Si-Cp)(OEt)$_3$);

(trifluorosilyl)cyclopentadienyl tris(n-propoxy) Hafnium (IV) (Hf(F$_3$Si-Cp)(OnPr)$_3$);

(trifluorosilyl)cyclopentadienyl tris(isopropoxy) Hafnium (IV) (Hf(F$_3$Si-Cp)(OiPr)$_3$);

(trifluorosilyl)cyclopentadienyl tris(tert-butoxy) Hafnium (IV) (Hf(F$_3$Si-Cp)(OtBu)$_3$);

(trifluorosilyl)cyclopentadienyl tris(sec-butoxy) Hafnium (IV) (Hf(F$_3$Si-Cp)(OsBu)$_3$);

(trifluorosilyl)cyclopentadienyl tris(n-butoxy) Hafnium (IV) (Hf(F$_3$Si-Cp)(OnBu)$_3$);

(trifluorosilyl)cyclopentadienyl tris(isobutoxy) Hafnium (IV) (Hf(F$_3$Si-Cp)(OiBu)$_3$);

(difluorosilyl)cyclopentadienyl tris(methoxy) Hafnium (IV) (Hf(F$_2$HSi-Cp)(OMe)$_3$);

(difluorosilyl)cyclopentadienyl tris(ethoxy) Hafnium(IV) (Hf(F$_2$HSi-Cp)(OEt)$_3$);

(difluorosilyl)cyclopentadienyl tris(n-propoxy) Hafnium (IV) (Hf(F$_2$HSi-Cp)(OnPr)$_3$);

(difluorosilyl)cyclopentadienyl tris(isopropoxy) Hafnium (IV) (Hf(F$_2$HSi-Cp)(OiPr)$_3$);

(difluorosilyl)cyclopentadienyl tris(tert-butoxy) Hafnium (IV) (Hf(F$_2$HSi-Cp)(OtBu)$_3$);

(difluorosilyl)cyclopentadienyl tris(sec-butoxy) Hafnium (IV) (Hf(F$_2$HSi-Cp)(OsBu)$_3$);

(difluorosilyl)cyclopentadienyl tris(n-butoxy) Hafnium (IV) (Hf(F$_2$HSi-Cp)(OnBu)$_3$);

(difluorosilyl)cyclopentadienyl tris(isobutoxy) Hafnium (IV) (Hf(F$_2$HSi-Cp)(OiBu)$_3$);

(monofluorosilyl)cyclopentadienyl tris(methoxy) Hafnium(IV) (Hf(FH$_2$Si-Cp)(OMe)$_3$);

(monofluorosilyl)cyclopentadienyl tris(ethoxy) Hafnium (IV) (Hf(FH$_2$Si-Cp)(OEt)$_3$);

(monofluorosilyl)cyclopentadienyl tris(n-propoxy) Hafnium(IV) (Hf(FH$_2$Si-Cp)(OnPr)$_3$);

(monofluorosilyl)cyclopentadienyl tris(isopropoxy) Hafnium(IV) (Hf(FH$_2$Si-Cp)(OiPr)$_3$);

(monofluorosilyl)cyclopentadienyl tris(tert-butoxy) Hafnium(IV) (Hf(FH$_2$Si-Cp)(OtBu)$_3$);

(monofluorosilyl)cyclopentadienyl tris(sec-butoxy) Hafnium(IV) (Hf(FH$_2$Si-Cp)(OsBu)$_3$);

(monofluorosilyl)cyclopentadienyl tris(n-butoxy) Hafnium(IV) (Hf(FH$_2$Si-Cp)(OnBu)$_3$);
(monofluorosilyl)cyclopentadienyl tris(isobutoxy) Hafnium(IV) (Hf(FH$_2$Si-Cp)(OiBu)$_3$);
(fluoro dimethylsilyl)cyclopentadienyl tris(methoxy) Hafnium(IV) (Hf(FMe$_2$Si-Cp)(OMe)$_3$);
(fluoro dimethylsilyl)cyclopentadienyl tris(ethoxy) Hafnium(IV) (Hf(FMe$_2$Si-Cp)(OEt)$_3$);
(fluoro dimethylsilyl)cyclopentadienyl tris(n-propoxy) Hafnium(IV) (Hf(FMe$_2$Si-Cp)(OnPr)$_3$);
(fluoro dimethylsilyl)cyclopentadienyl tris(isopropoxy) Hafnium(IV) (Hf(FMe$_2$Si-Cp)(OiPr)$_3$);
(fluoro dimethylsilyl)cyclopentadienyl tris(tert-butoxy) Hafnium(IV) (Hf(FMe$_2$Si-Cp)(OtBu)$_3$);
(fluoro dimethylsilyl)cyclopentadienyl tris(sec-butoxy) Hafnium(IV) (Hf(FMe$_2$Si-Cp)(OsBu)$_3$); (fluoro dimethylsilyl)cyclopentadienyl tris(n-butoxy) Hafnium(IV) (Hf(FMe$_2$Si-Cp)(OnBu)$_3$); (fluoro dimethylsilyl)cyclopentadienyl tris(isobutoxy) Hafnium(IV) (Hf(FMe$_2$Si-Cp)(OiBu)$_3$); (tris(trifluoromethyl)silyl)cyclopentadienyl tris(methoxy) Hafnium(IV) (Hf((CF$_3$)$_3$Si-Cp)(OMe)$_3$); (tris(trifluoromethyl)silyl)cyclopentadienyl tris(ethoxy) Hafnium(IV) (Hf((CF$_3$)$_3$Si-Cp)(OEt)$_3$); (tris(trifluoromethyl)silyl)cyclopentadienyl tris(n-propoxy) Hafnium(IV) (Hf((CF$_3$)$_3$Si-Cp)(OnPr)$_3$); (tris(trifluoromethyl)silyl)cyclopentadienyl tris(isopropoxy) Hafnium(IV) (Hf((CF$_3$)$_3$Si-Cp)(OiPr)$_3$);
(tris(trifluoromethyl)silyl)cyclopentadienyl tris(tert-butoxy) Hafnium(IV) (Hf((CF$_3$)$_3$Si-Cp)(OtBu)$_3$); (tris(trifluoromethyl)silyl)cyclopentadienyl tris(sec-butoxy) Hafnium(IV) (Hf((CF$_3$)$_3$Si-Cp)(OsBu)$_3$); (tris(trifluoromethyl)silyl)cyclopentadienyl tris(n-butoxy) Hafnium(IV) (Hf((CF$_3$)$_3$Si-Cp)(OnBu)$_3$); (tris(trifluoromethyl)silyl)cyclopentadienyl tris(isobutoxy) Hafnium(IV) (Hf((CF$_3$)$_3$Si-Cp)(OiBu)$_3$);
(bis(trifluoromethyl)silyl)cyclopentadienyl tris(methoxy) Hafnium(IV) (Hf((CF$_3$)$_2$HSiCp)(OMe)$_3$); (bis(trifluoromethyl)silyl)cyclopentadienyl tris(ethoxy) Hafnium(IV) (Hf((CF$_3$)$_2$HSi-Cp)(OEt)$_3$); (bis(trifluoromethyl)silyl)cyclopentadienyl tris(n-propoxy) Hafnium(IV) (Hf((CF$_3$)$_2$HSi-Cp)(OnPr)$_3$); (bis(trifluoromethyl)silyl)cyclopentadienyl tris(isopropoxy) Hafnium(IV) (Hf((CF$_3$)$_2$HSi-Cp)(OiPr)$_3$);
(bis(trifluoromethyl)silyl)cyclopentadienyl tris(tert-butoxy) Hafnium(IV) (Hf((CF$_3$)$_2$HSi-Cp)(OtBu)$_3$); (bis(trifluoromethyl)silyl)cyclopentadienyl tris(sec-butoxy) Hafnium(IV) (Hf((CF$_3$)$_2$HSi-Cp)(OsBu)$_3$); (bis(trifluoromethyl)silyl)cyclopentadienyl tris(n-butoxy) Hafnium(IV) (Hf((CF$_3$)$_2$HSi-Cp)(OnBu)$_3$); (bis(trifluoromethyl)silyl)cyclopentadienyl tris(iso-butoxy) Hafnium(IV) (Hf((CF$_3$)$_2$HSi-Cp)(OiBu)$_3$);
((trifluoromethyl)dimethylsilyl)cyclopentadienyl tris(methoxy) Hafnium(IV) (Hf((CF$_3$)Me$_2$-Cp)(OMe)$_3$); ((trifluoromethyl)dimethylsilyl)cyclopentadienyl tris(ethoxy) Hafnium(IV) (Hf((CF$_3$)Me$_2$-Cp)(OEt)$_3$); ((trifluoromethyl)dimethylsilyl)cyclopentadienyl tris(n-propoxy) Hafnium(IV) (Hf((CF$_3$)Me$_2$-Cp)(OnPr)$_3$); ((trifluoromethyl)dimethylsilyl)cyclopentadienyl tris (isopropoxy) Hafnium(IV) (Hf((CF$_3$)Me$_2$-Cp)(OiPr)$_3$); ((trifluoromethyl)dimethylsilyl)cyclopentadienyl tris(tert-butoxy) Hafnium(IV) (Hf((CF$_3$)Me$_2$-Cp)(OtBu)$_3$); ((trifluoromethyl)dimethylsilyl)cyclopentadienyl tris (sec-butoxy) Hafnium(IV) (Hf((CF$_3$)Me$_2$-Cp)(OsBu)$_3$); ((trifluoromethyl)dimethylsilyl)cyclopentadienyl tris(n-butoxy) Hafnium(IV) (Hf((CF$_3$)Me$_2$-Cp)(OnBu)$_3$); and ((trifluoromethyl)dimethylsilyl)cyclopentadienyl tris(isobutoxy) Hafnium(IV) (Hf((CF$_3$)Me$_2$-Cp)(OiBu)$_3$).

7. The Hafnium-containing film forming composition of claim 6, wherein the precursor is (trimethylsilyl)cyclopentadienyl tris(iso-propoxy) Hafnium(IV) [Hf(TMS-Cp)(OiPr)$_3$].

8. The Hafnium-containing film forming composition of claim 1, the composition comprising between approximately 95% w/w and approximately 100% w/w of the precursor.

9. The Hafnium-containing film forming composition of claim 1, the composition comprising between approximately 0.0% w/w and approximately 5.0% w/w impurities.

10. The Hafnium-containing film forming composition of claim 9, the impurities including alcohol; alkylamines; dialkylamines; alkylimines; cyclopentadiene; dicyclopentadiene; alkygermane; THF; ether; pentane; cyclohexane; heptanes; benzene; toluene; chlorinated metal compounds; lithium, sodium, or potassium alkylamido; lithium, sodium, or potassium alkoxy; and/or lithium, sodium, or potassium cyclopentadienyl.

11. The Hafnium-containing film forming composition of claim 1, the composition comprising between approximately 0 ppbw and approximately 1 ppmw metal impurities.

12. The Hafnium-containing film forming composition of claim 11, the metal impurities including Aluminum (Al), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Zirconium (Zr), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Titanium (Ti), Uranium (U), and/or Zinc (Zn).

13. A process for the deposition of a Hafnium-containing film on a substrate, the process comprising the steps of: introducing a vapor of the Hafnium-containing film forming composition of any one of claims 1 to 12 into a reactor having a substrate disposed therein and depositing at least part of the Silicon- and Hafnium-containing precursor onto the substrate.

14. The process of claim 13, further comprising introducing at least one reactant into the reactor, wherein the reactant is selected from the group consisting of H$_2$, H$_2$CO N$_2$H$_4$, NH$_3$, SiH$_4$, Si$_2$H$_6$, Si$_3$H$_8$, SiH$_2$Me$_2$, SiH$_2$Et$_2$, N(SiH$_3$)$_3$, hydrogen radicals thereof, and mixtures thereof.

15. The process of claim 13, further comprising introducing at least one reactant into the reactor, wherein the reactant is selected from the group consisting of:
O$_2$, O$_3$, H$_2$O , H$_2$O$_2$ NO, N$_2$O, NO$_2$, oxygen radicals thereof, and mixtures thereof.

* * * * *